United States Patent [19]

Smyser et al.

[11] Patent Number: 5,904,639
[45] Date of Patent: May 18, 1999

[54] APPARATUS, SYSTEM, AND METHOD FOR CARRYING OUT PROTOCOL-BASED ISOMETRIC EXERCISE REGIMENS

[75] Inventors: Michael A. Smyser, Galena; David W. Ferguson, Pickerington, both of Ohio

[73] Assignee: MD Systems, Westerville, Ohio

[21] Appl. No.: 09/036,051

[22] Filed: Mar. 6, 1998

[51] Int. Cl.⁶ .................................................. A61B 5/103
[52] U.S. Cl. ................................. 482/91; 601/23; 482/1; 482/5; 600/595
[58] Field of Search .................... 482/1–9, 91, 900–902; 600/481, 483, 488, 595; 601/23, 33, 40

[56] References Cited

U.S. PATENT DOCUMENTS

| | | | |
|---|---|---|---|
| 5,163,443 | 11/1992 | Fry-Welch | 600/595 |
| 5,435,315 | 7/1995 | McPhee | 600/483 |
| 5,720,711 | 2/1998 | Bond et al. | 601/23 |

*Primary Examiner*—Glen E. Richman
*Attorney, Agent, or Firm*—Mueller and Smith, LPA

[57] ABSTRACT

A protocol-configurable isometric hand grip recording dynamometer with user guidance. The apparatus employs a grip within which is mounted a load cell. The load cell, in turn, is coupled to a rigid printed circuit board which is compressively squeezed during an exercise regimen. A readout is integrally formed with the battery operated system to provide aural and visual cuing at an angle facilitating the user's reading of a display. Visual cues are provided at the display throughout an exercise regimen prompting the user as to which hand to use and the amount of compressive squeezing force to be applied. The system and method includes a technique for scoring the efforts of the user. The microprocessor-driven device includes archival memory and a data communications port such that may be employed interactively with a trainer or physician.

36 Claims, 22 Drawing Sheets

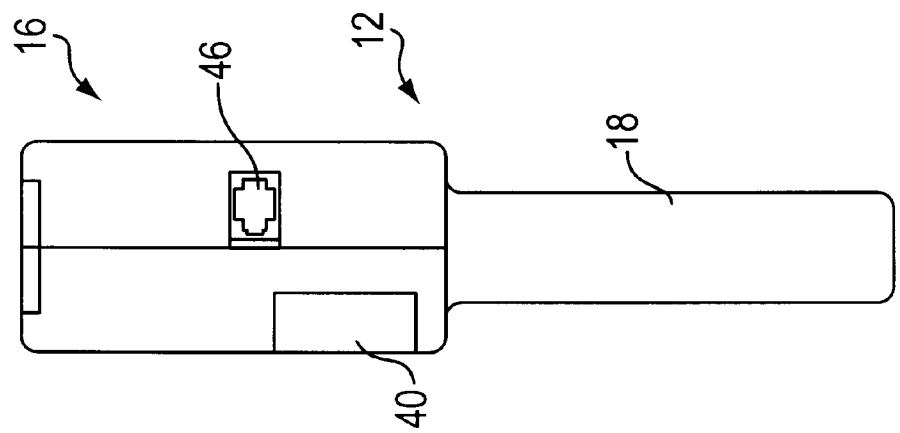
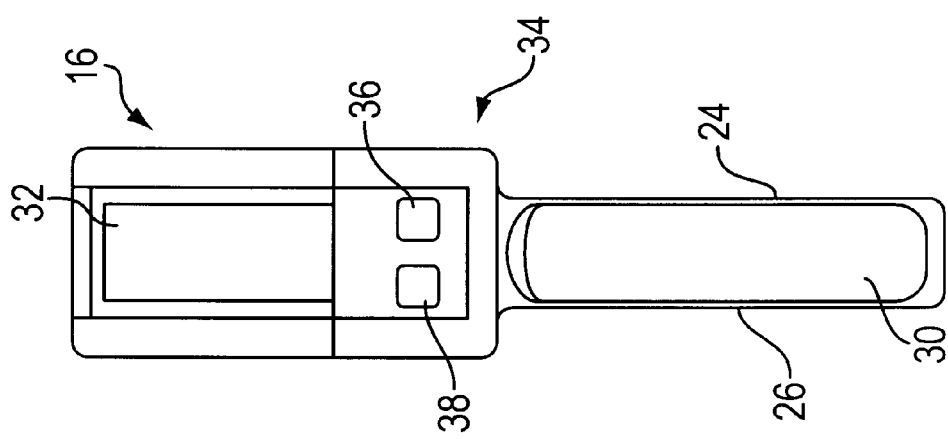
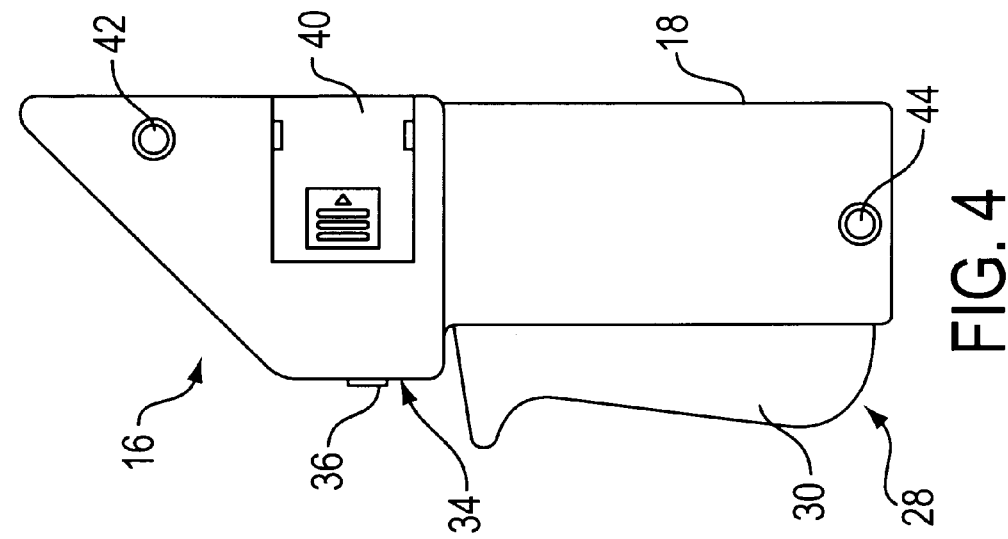

APPARATUS, SYSTEM, AND METHOD FOR CARRYING OUT PROTOCOL-BASED ISOMETRIC EXERCISE REGIMENS

CROSS-REFERENCE TO RELATED APPLICATIONS

STATEMENT REGARDING FEDERALLY SPONSORED RESEARCH

Not applicable.

BACKGROUND OF THE INVENTION

The present invention relates to the field of blood pressure and more particularly to an apparatus and method for safely reducing the resting blood pressure (both systolic and diastolic pressures) of humans and especially for those humans who are hypertensive.

Buck, et al., "Isometric Occupational Exercise and the Incidence of Hypertension", *J. Occup. Med.*, 27:370–372, 1985, show a practical application of the principle of isometric exercise influencing blood pressure. The incidence of hypertension was lower in individuals engaged in occupations that had higher components of isometric efforts. A subtle, but significant, feature of this paper is that the original hypothesis was that, since blood pressure rises during an isometric effort, a job that required repeated isometric efforts might have an accumulative effect and contribute to a sustained elevation of blood pressure. However, the investigation reported showed just the opposite result.

Choquette, et al., "Blood Pressure Reduction in 'Borderline' Hypertensives Following Physical Training", *Can. Med. Assoc. J.*, 1108:699–703, 1973, show a comparison between rhythmic and isometric exercise. While these authors showed an effect of exercise on lowering resting blood pressure, the present invention which utilizes isometric exercise lowers the blood pressure even more. Further, it has been well documented that compliance (staying with the treatment) is rather poor for rhythmic exercise. A greater percentage of people who run, jog, cycle, swim, or the like, to achieve fitness, simply quit.

Clarke, et al., "The Duration of Sustained Contractions of the Human Forearm at Different Muscle Temperatures", *J. Physiol.*, 143:454–473, 1958, show an early hand grip dynamometer which is used by patients whose arms are immersed in water for measuring the duration of sustained contractions of the human form at different muscle temperatures.

Gilders, et al., "Endurance Training and Blood Pressure in Normotensive and Hypertensive Adults", *Med. Sci. Sports. Exerc.*, 21:629–636, 1989, report a study that indicates that endurance training of the rhythmic or aerobic type does not have the benefit of lowering blood pressure, for either subjects starting with normal or with hypertensive blood pressures.

Hagberg, et al., "Effective Weight Training on Blood Pressure and Hemodynarnics in Hypertensive Adolescents", *J. Pediatr.*, 1104:147–151, 1984, show that weightlifting, which has a major isometric component, although not a "pure" isometric effort, can keep blood pressure down after it was lowered by rhythmic training.

Harris, et al., "Physiological Response to Circuit Weight Training in Borderline Hypertensive Subjects", *Med. Sci. Spots Exerc.*, 19:246–252, 1987, and Hurley, et al., "Resistive Training Can Induce Coronary Risk Factors Without Altering $VO_{2mx}$ or Percent Body Fat", *Med. Sci. Sports Exerc.*, 20:150–154, 1988, both deal with resistive training similar to the Hagberg, et al., publication in which there is movement, hence rhythmic effort, but where much weight is being moved, hence, "resistive" effort. This is interpreted to mean that in such a "mixed" effort, with both rhythmic and isometric components, that the isometric component is providing the real benefit in lowering resting blood pressure. In both of these papers, $VO_{2max}$ does not change. The measure of change of $VO_{2max}$ is one associated with improvement of endurance seen with rhythmic exercise. The point, then, supports contentions about isometric exercise in that resistive efforts which have a major isometric component, do not show the kind of change in $VO_{2max}$ seen typically with rhythmic or endurance exercise, yet do show the kind of lowering of resting blood pressure, though not as much, as can be obtained with only isometric exercise.

It has been reported that a reduction in blood pressure reduces the incidence of mortality in the report, Hypertension Detection and Follow-up Program Cooperative Group, "The Effect of Treatment on Mortality in 'Mild' Hypertension", *N. Engl. J. Med.*, 307:976–980, 1982. In an early paper, Kiveloff, et al., "Brief Maximal Isometric Exercise in Hypertension", *J. Am. Geriatr. Soc.*, 9:1006–1012, 1971, suggest that isometric exercise can lower blood pressure in humans. No device was used in which to perform the isometric effort, rather subjects just stood and contracted muscles of the body. No quantitative measure of the amount of isometric effort is reported. Merideth, et al., "Exercise Training Lowers Resting Renal but not Cardiac Sympathetic Activity in Humans", *Hypertension*, 18:575–582, 1991, present evidence that rhythmic exercise results in a reduction of peripheral resistance, i.e., a "relaxation" of blood vessels in the body, which would result in the lowering of blood pressure within them.

Seals and Hagberg, "The Effect of Exercise Training on Human Hypertension: A Review", *Med. Sci. Sports Exerc.*, 16:207–215, 1984, reviews 12 earlier investigations of rhythmic exercise studies.

Tipton, "Exercise, Training and Hypertension: An Update", *Exerc. Sport Sci., Rev.*, vol. 19, Ch. 13, 1991, pp 447–505, is one of the most comprehensive recent reviews of the state of the art on the effect of exercise on blood pressure. At page 473, Tipton refers to a study which included "circuit training" which has a significant isometric component and which showed a lowering of blood pressure. The author also refers to one of his own studies with rats which were made to perform a type of isometric exercise in which the rats "unexpectedly" did not experience an increase in blood pressure as the authors had predicted would happen.

Thus, the art makes clear that a lowering of resting blood pressure is beneficial to humans in general and is particularly important to those humans who are hypertensive. While isometric and rhythmic (or dynamic) exercise is beneficial to humans in general, the isometric component of exercise, according to the foregoing art, appears to contribute more significantly to the lowering of resting blood pressure. This speculation was confirmed by studies optimizing an isometric regimen to be performed by patients. See in this regard, Wiley, et al. "Isometric Exercise Training Lowers Resting Blood Pressure", Med. Sci. Sports Exerc. 24(7):749–754, 1992. Such procedure and apparatus for carrying it out are described in U.S. Pat. No. 5,398,696, entitled "Isometric Exercise Method for Lowering Resting Blood Pressure and Grip Dynamometer Useful Therefor" by Wiley, issued Mar. 21, 1995, assigned in common herewith, and incorporated herein by reference.

With the establishment of this basic isometric-based technology, investigators have observed a need for developing a corresponding apparatus and system which will encourage the patient to carry out a specified isometric regimen with consistency over extended periods of time. Such instrumentation must, therefore, be small, conveniently portable, and highly reliable. Because the regimen requires the application of hand-grip forces corresponding with the maximum capability of the user, the necessarily diminutive instrument additionally is called upon to sustain the application of substantial pressures. Of further importance, it is necessary that grip forces be measured with substantial accuracy. To promote patient use, necessary data inputting as well as the computation of target force values and the carrying out of prescribed timing requires computer-based automation. Visual and aural prompts as well as perceptible feedback representing the quality of performance by the user is called for, as well as a capability for the archiving or logging of performance data. Of further importance, the instrument should be capable of interactive communication not only with the user but with the attending physician or trainer, thus calling for a downloading and programming feature for patient management and/or training evaluation.

BRIEF SUMMARY OF THE INVENTION

The present invention is addressed to a compact, lightweight isometric apparatus which exhibits a structural configuration enabling it to be subjected to substantial squeezing induced loadings. Having a handle or grip which incorporates a load cell assembly, the design of the instrument employs a rigid polymeric circuit board as a compression component positioned between the load cell assembly and an oppositely disposed gripping surface. Extending from a hand grip is a liquid crystal display and two user actuated control switches or buttons. The display is mounted in sloping fashion with respect to the grip such that the user can observe important visual cues while carrying out an exercise regimen.

The control circuit incorporated with the instrument is microprocessor driven and includes a non-volatile archival memory, as well as a battery powered date and time component. External communication with the instrument is made available through a communications port such that the device may be configured by programming and, additional data such as blood pressure values and the like may be inserted into its archival memory from an external device.

The system and method associated with the instrument provide important visual and aural cuing to the user and additionally, through the utilization of a unique scoring technique, provide user performance data for training or patient management purposes. Visual cuing not only guides the user through a multi-step protocol designed to lower blood pressure levels, but also aids the user in maintaining pre-computed target level grip compression levels. For instance, during a measured interval wherein target level gripping compression is called for, a dynamic bar graph in combination with a center pointer at the display shows the user the relative accuracy of the compressive grip which is being asserted. Where the grip is excessive beyond an upper threshold limit, the user is provided with an aural warning. Conversely, where the user's grip is not sufficient to reach target load values, then the display transitions from a steady state readout to one which blinks. Similarly, during maximum effort (MVC) intervals, a dynamic bar graph gives the user visual information as to the increasing or decreasing value of compressive grip force. The instrument also may be custom programmed for individual users who are identified in connection with a selection and menu switching arrangement.

Other objects of the invention will, in part, be obvious and will, in part, appear hereinafter.

The invention, accordingly, comprises the apparatus, system, and method possessing the construction, combination of elements, arrangement of parts and steps which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 4 is a right side view of the apparatus of FIG. 1;

FIG. 5 is a top view of the apparatus of FIG. 1;

FIG. 6 is a bottom view of the apparatus of FIG. 1;

DETAILED DESCRIPTION OF THE INVENTION

Figure 1:
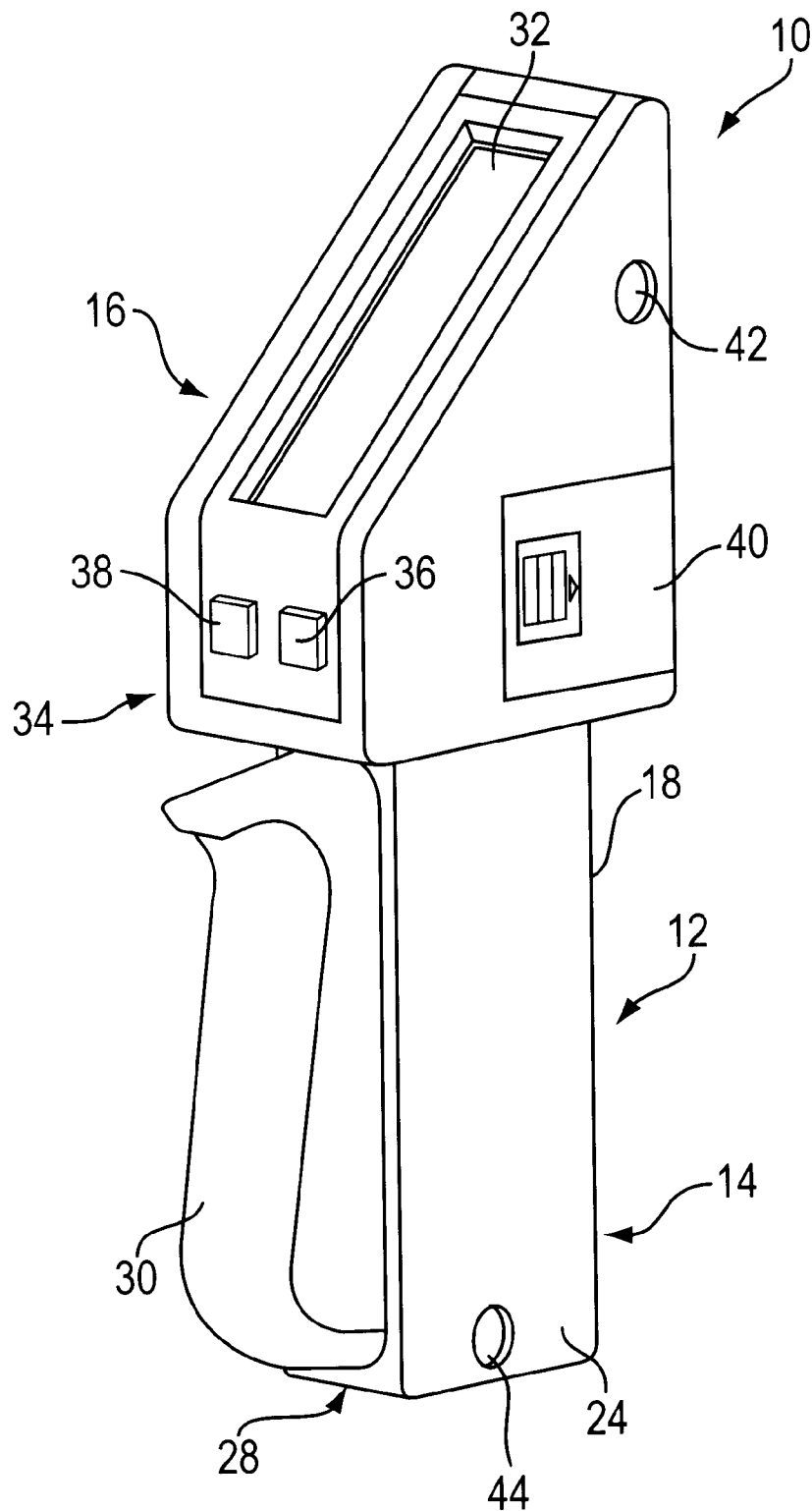
FIG. 1 is a perspective view of apparatus according to the invention.
Figure 2:
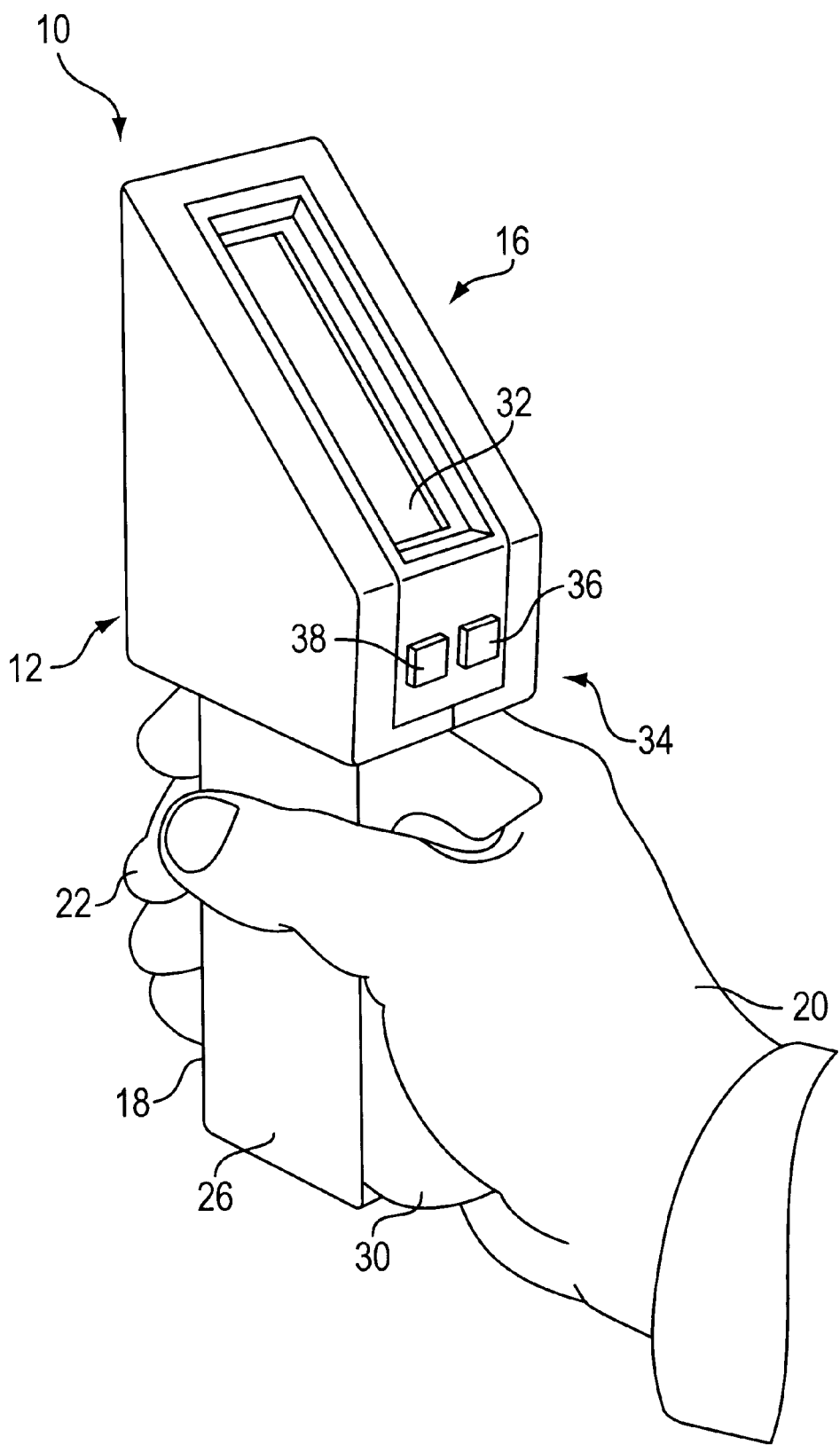
FIG. 2 is a perspective view of the apparatus of FIG. 1 and showing its being gripped by a user.

The protocol configurable isometric exercise apparatus of the invention is lightweight, portable, battery powered, and sufficiently rugged to withstand the compressive pressures which it necessarily endures during use. Looking to FIG. 1, the instrument or apparatus is represented generally at 10 as having a housing represented generally at 12. This housing is formed of acrylonitrile butadiene styrene (ABS) and, thus, is resistant to impacts and securely retains the internal components thereof. FIG. 1 shows that the housing 12 includes a hand-grasping portion 14 and an interacting portion 16 which supplies, inter alia, prompts or cues to the user in carrying out a regimen or protocol. The hand grasping portion 14 includes a hand graspable portion 18 which is of curved surface configuration so as to provide a multiple finger receiving surface. This surface is seen in FIG. 2 in conjunction with the hand 20 of a user, the forward finger regions 22 of which are wrapped around the curved surface. Hand grasping portion 14 includes oppositely disposed sides, one of which is seen at 24 in FIG. 1, and the opposite one of which is seen at 26 in FIG. 2. Sides 24 and 26 extend to another hand graspable portion represented generally at 28 which will be seen to have an outwardly disposed load input opening formed therein. Over that opening there is positioned a polymeric hand grip 30. Hand grip 30 is formed, for example, of a flexible polymeric material such as Santopren No. 101–64, a thermoplastic elastomer, marketed by General Polymers of Charlotte, N.C. The grip 30 covers a load cell assembly such that the user may squeeze the hand grasping portion 14 by holding it as shown in FIG. 2. Note that the hand grip 30 is formed with the shape of a pistol grip to facilitate the compressive squeezing exercise regimen which is carried out with device 10. The interacting portion 16 includes a readout assembly provided as a liquid crystal display (LCD) 32. Looking additionally to FIG. 5, adjacent to the display 32 is an input portion represented generally at 34 which extends in adjacency from the hand grip portion grasping portion 14 and is seen to incorporate two finger actuable switches 36 and 38. These switches are covered with a flexible polymeric material such as the noted Santoprene. The LCD or readout assembly 32 is seen to be provided at a reading angle or slope such that the LCD 32 is readily observable by the user during an exercise regimen. This is demonstrated in FIG. 2, the 45° angle at which the display is sloped being readily perceived in conjunction with FIG. 4. FIG. 1 further reveals that the forward interacting portion 16 includes a battery compartment which is closed by a thumb actuated battery door 40. In general, the housing 12 is formed of the battery door 40 and three additional pieces which are held together by three screws, two of which are mounted within cylindrical screw cavities 42 and 44. Preferably, the cavities are capped with plastic inserts such that a substantial effort is required to open up the housing 12. This provides a high degree of protection from tampering and accidental damage to the electronic components within housing 12. Looking additionally to FIG. 6, the bottom of the housing 12 is seen to provide a communications port 46 through which the apparatus 10 may be programmed from, for example, a personal computer. Additionally, the communications port 46 provides for downloading of stored exercise data to a data receiving facility.

Figure 3:
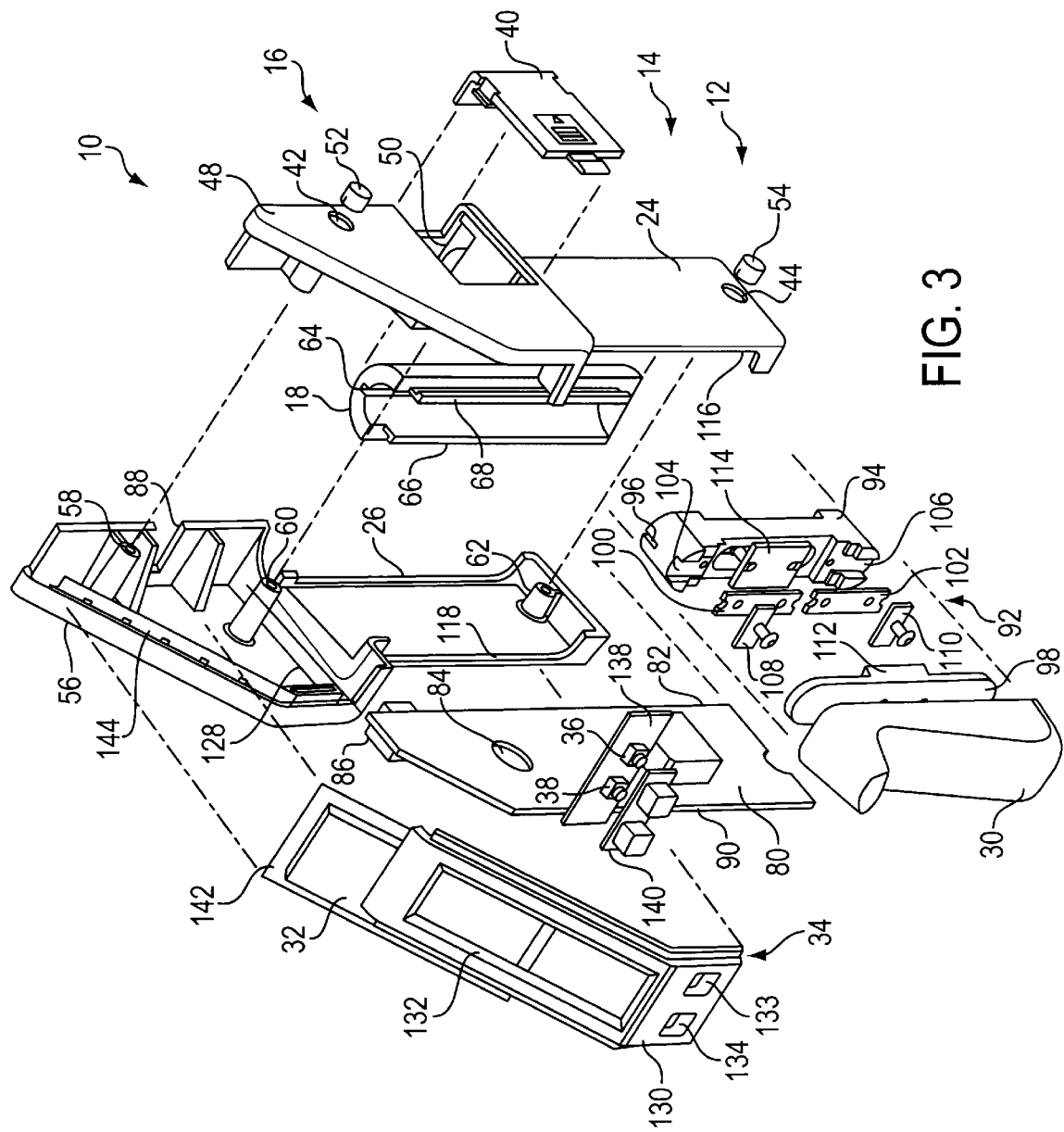
FIG. 3 is an exploded perspective view of the apparatus of FIG. 1.

Looking to FIG. 3, an exploded perspective view of the apparatus 10 is provided. In the figure, the side 24 of gripping portion 14 is seen to be integrally molded with the side 48 and one-half of the bottom of interacting portion 16. Battery door 40 is seen to cover a battery compartment represented at 50. Plastic inserts or plugs are shown at 52 and 54 which are insertable within the earlier-noted respective screw cavities 42 and 44. Left side 26 of the hand gripping portion 14 is seen to be integrally molded with the side and the bottom portion 56 of interacting portion 16. Also located internally at side 56 are two screw receiving posts 58 and 60. The third such post is provided internally at side 26 as represented at 62. Post 58 receives a screw inserted through the cavity 42, while post 60 receives a screw which is inserted from the back of the battery cavity 50. Post 62 receives a third screw which is inserted within the screw compartment 44. Those three screws hold the entire assemblage together. At the bottom of the hand graspable portion 14 is the noted hand graspable portion 18 having a curved multiple finger receiving surface which extends outwardly from sides 24 and 26. Note, in particular, that this component 18 is formed having an elongate alignment channel 64 extending along its internal length. The component 18 additionally is retained upon the sides 24 and 26 by the L-shaped connectors 66 and 68.

Disposed centrally within the cavity defined by the sides 24 and 26 is a printed circuit board or rigid circuit supporting panel 80. The lower edge 82 of the circuit board 80 is positioned within the alignment channel 64 which functions, inter alia, to prevent the board or panel 80 from flexing along its length. Board 82 carries essentially all of the control circuitry including microprocessor, analog-to-digital converter, buffer filters, and the like. It is formed with a circular opening 84 which functions to carry battery power supply cable to the battery compartment 50. Note, additionally, that a communications port component 86 is mounted to the circuit board 80 and extends to a port opening 88 formed in the bottom of side 56. The communications protocol is RS-485, balanced simplex communications.

Mounted upon the opposite or uppermost edge 90 of circuit board 80 is a load cell assembly represented generally at 92. Load cell assembly 92 includes an elongate base 94 having slots positioned at either end, one of which is shown at 96. These slots are positioned over the upper edge 90 of circuit board 80. It may be observed that compressive squeezing force is transmitted from the base 94 into the circuit board 80 an is counter-acted by the finger receiving component 18 at slot 64. Assembly 92 further includes an elongate outer force component 98. Two steel plate-form load cells 100 and 102 are mounted from load cell mount structures shown, respectively, at 104 and 106, formed within base 94. Such mounting is in cantilever fashion, the load cell 100 being attached to mount 104 by a screw and mounting plate assembly 108. Similarly, load cell 102 is attached in cantilever fashion to mount structure 106 by a screw and mounting plate assembly 110. Outer force component 98 is seen to have a centrally disposed rectangular post portion 112 which is attached by a connector plate to the mutually inwardly extending ends of the load cells 100 and 102. The attachment plates for this union are seen at 114. Screws are used to effect the attachment. The hand grip 30 is flexible and is formed having an interior cavity which fits down over the force component 98 and a portion of base 94 when the apparatus 10 is assembled. The load cell assembly 94 protrudes through an outwardly disposed load input opening formed between sides 24 and 26. The edges thereof are seen respectively at 116 and 118.

A fourth housing component is the interacting portion 16 top cover 130. Formed as the other components of ABS plastic, the cover 130 includes a rectangular bezel opening 132 within which the LCD 32 is positioned. Input portion 34 is formed with the cover 130. It may be noted that two rectangular openings 133 and 134 are located within that portion of cover 130. The switching function is mounted on a separate circuit board 138 which is seen to carry two push actuated switches as earlier described at 36 and 38, and identified by the same numeration in this figure. Located, in turn, over the switches 36 and 38 is a flexible polymeric cover formed of the earlier-noted Santoprene and seen at 140. Connection between the circuit board 138 and the control circuitry mounted upon circuit board 80 is by a flexible bus (not shown). Circuit board 138 is supported between two slots formed in the interior of sides 48 and 56. One of these slots is seen at 128. The LCD 32 is seen mounted upon a circuit board 142 which, in turn, is supported by ledge-like structures formed in the interior of sides 48 and 56. In this regard, one such ledge-like structure is represented at 144. Communication between the LCD 32 and the control circuitry at circuit board 80 also is by a flexible bus. Thus, none of the forces involved with the board 80 and its associated squeeze-related components is transmissible to either the circuit board 138 carrying switches 36 and 38, or the circuit board 142 carrying the LCD readout 32.

Figure 7:
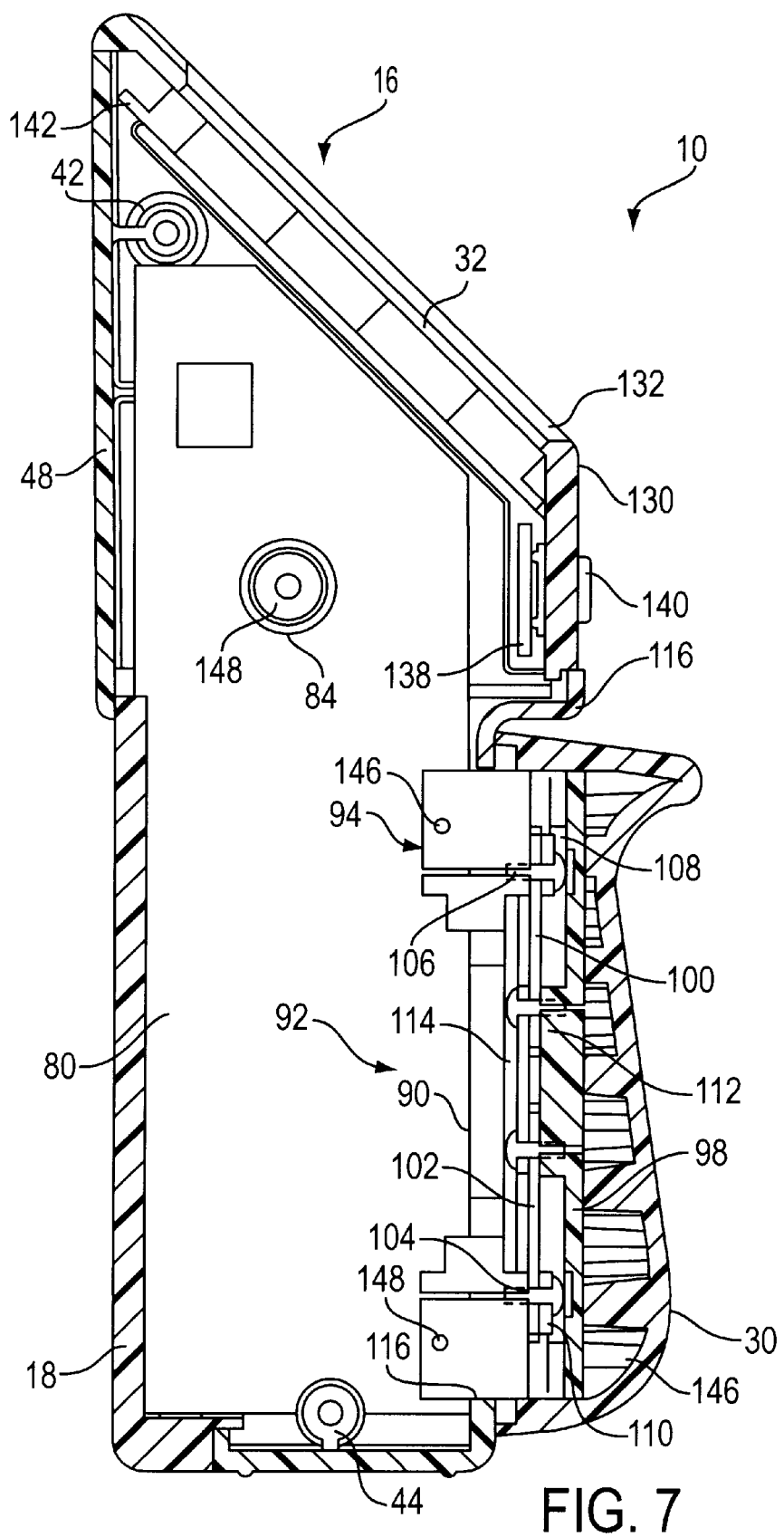
FIG. 7 is a sectional view of the apparatus of FIG. 1 looking toward its right side from its left side.
Figure 8:
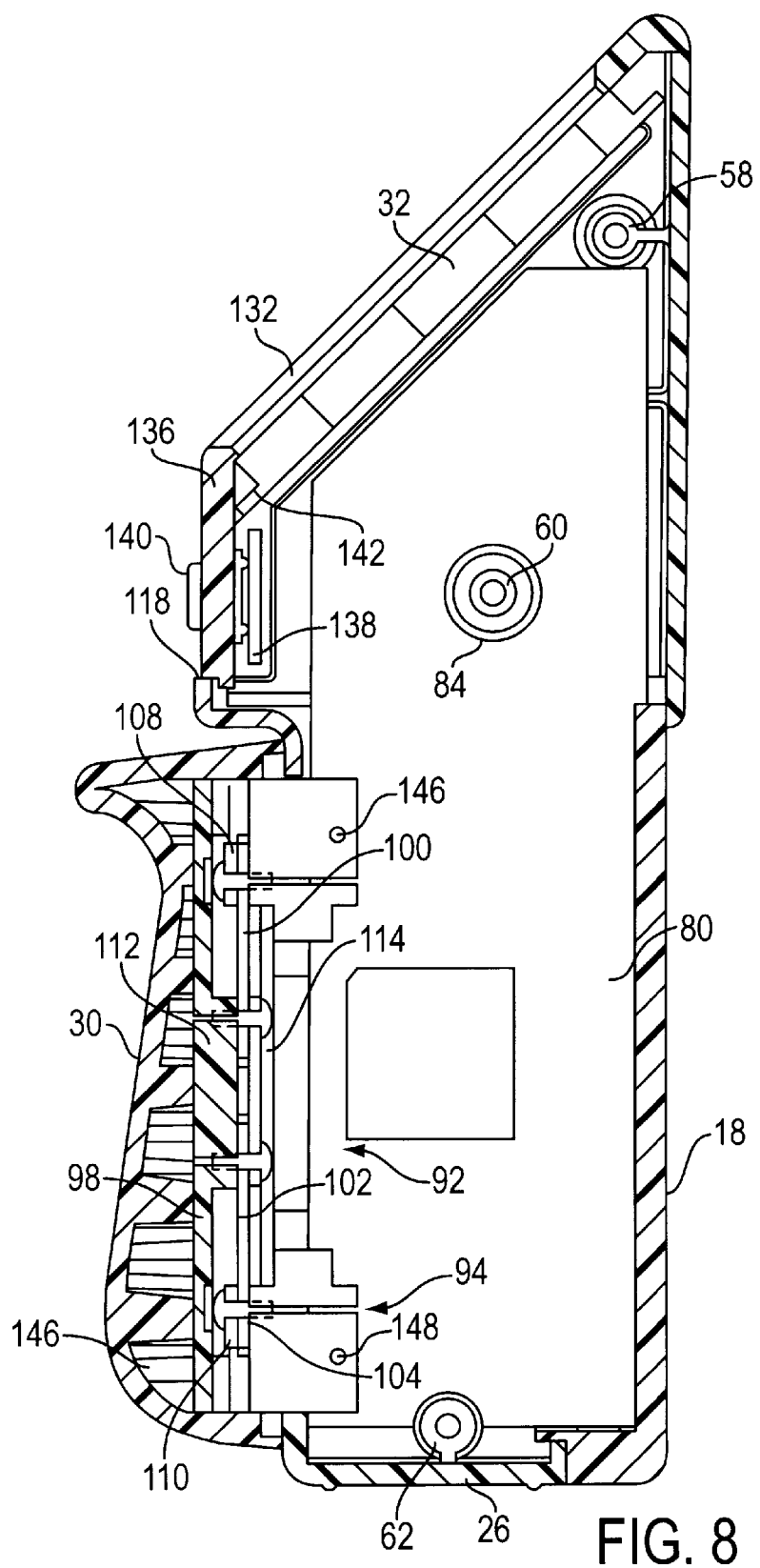
FIG. 8 is a sectional view of the apparatus of FIG. 1 looking toward its left side from its right side.

Referring additionally to FIGS. 7 and 8, the interior cavities of the apparatus 10 are further illustrated. In the figures, FIG. 7 is a sectional view from the left side of the apparatus 10. Thus, side components 24 and 48 are seen in section. Conversely, in FIG. 8, a sectional view is provided looking toward the left side components 26 and 56. Thus, the left side components are seen in section. In the figures, two bores are seen to be provided in the base 94 of the load cell assembly 92. Note that those of at the end portions of the base 94 extend below the top edge 90 of circuit board 80. As such, the edge 90 protrudes into slots, one of which is described at 96 in FIG. 3. To secure the base 94 to the circuit board 80, pins or pin structures are provided which extend through small bores 146 and 148. These figures also reveal that the cover or hand grip 30 is configured having an inwardly-disposed cavity, portions of which are seen at 146. The cover slides down over the upper portion of the load cell assembly 92 such that its flexible edges cover the opening defined by edges 116 and 118. To accommodate for variations in hand size, different sizes of hand grip 30 are available to the user. From the figures, it is apparent that squeezing compressive force applied between the hand grip 30 and the hand graspable portion 18 is asserted through the load cell assembly 92 and compressively onto the edge of circuit board 80. Opposing force from the hand then is asserted via portion 18 into the circuit board 80. Because the board 80 remains aligned and unwarped by virtue of its mounting, for example within channel 64 (FIG. 3) and by virtue of the slot mounting of base 94 of load cell assembly 92, the compressive forces are readily accommodated by this circuit board. FIG. 7 shows the screw cavities 42 and 44 as well as a screw cavity 148 which extends from the inside of the battery compartment 50. A screw inserted from cavity 148 engages the screw receiving post 60 seen in FIG. 8. Similarly, a screw inserted within cavity 44 engages the post 62 seen in FIG. 8 and a screw inserted in the cavity 42 engages the post 58 seen in FIG. 8.

Figure 9:
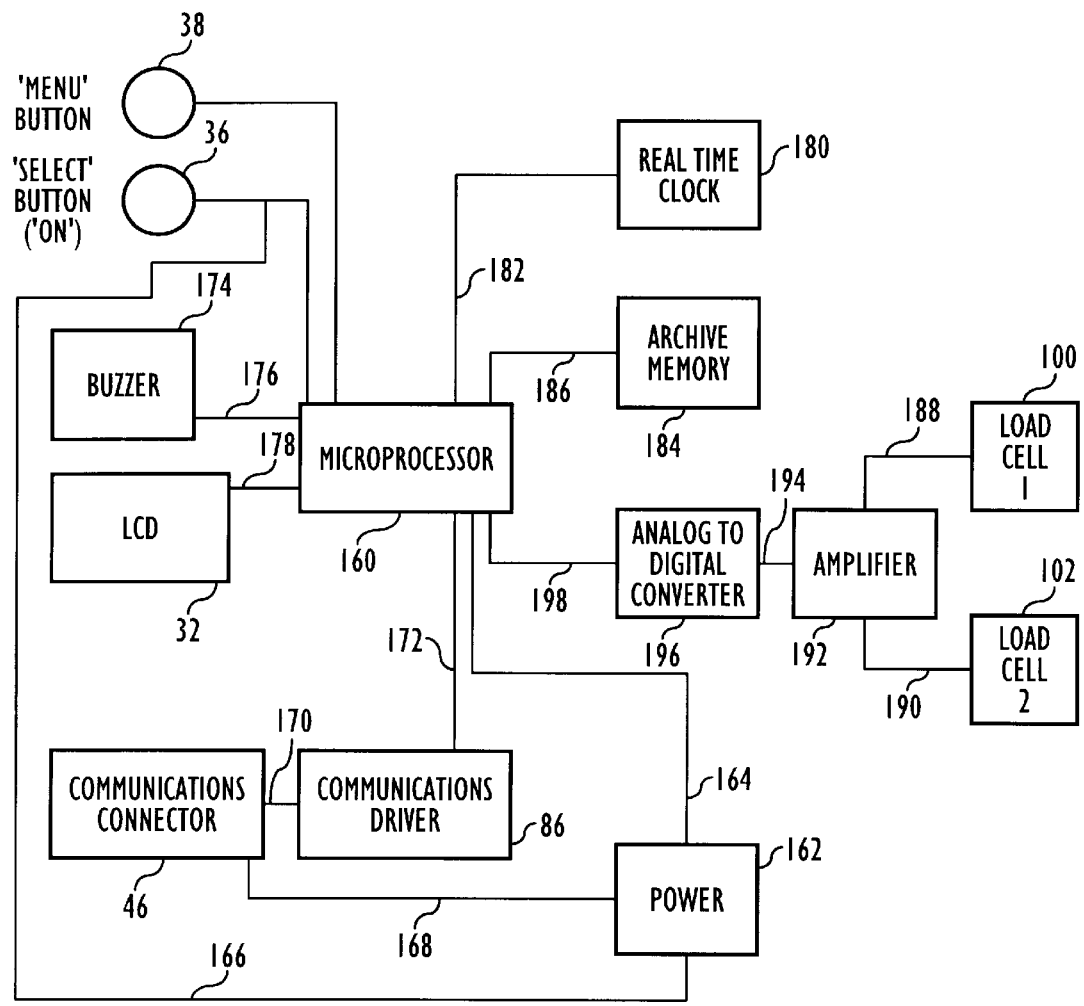
FIG. 9 is a block diagrammatic drawing of the circuit employed with the apparatus of FIG. 1.

Turning to FIG. 9, a block diagrammatic representation of the controller components of the device 10 is revealed. In general, the device or apparatus 10 is microprocessor driven, for example employing a type 8051 microprocessor as represented at block 160. The controller is powered by a standard 9 v battery. That voltage then is regulated to 5 v for use by the circuit components. The power supply to the strain gauge implemented load cells 100 and 102 is dropped by a resistor such that the maximum current applied is limited to 50 milliamps. Such power supply is represented in the figure at block 162 which, in turn, is seen to be associated with microprocessor 160 via line 164 and with switch 36 via line 166. In this regard, the switches 36 and 38 respectively are labeled "select" and "menu". Switch 36 serves the additional function of an on switch. Power also is seen to be supplied to the communications connector 46 as represented at line 168. Communications connector 46, in turn, is seen coupled to a communications driver 86 as represented at line 170. Driver 86 is seen associated with the microprocessor 160 as represented by line 172. Microprocessor 160 also provides control over an annunciator or buzzer represented at block 174 and line 176. Similarly, control to the liquid crystal display (LCD) 32 from microprocessor 160 is represented at line 178. A real time clock is provided with the controller circuit as represented at block 180. Time and date data from that clock is used in conjunction with the monitoring and memory features of the apparatus 10 such that important data, including date and time of a given exercise regimen can be retained in memory and downloaded via the communications port when called for. The association of the real time clock function 180 and microprocessor 160 is represented at line 182. Archival memory as well as temporary memory are provided with the circuit. Archival memory may be provided, for example, as an electrically erasable programmable read only memory (EEPROM) an 8 kilobyte device which requires no power to sustain its memory retention, i.e. it is non-volatile. The archival memory as represented at block 184 in its association with the microprocessor 160 is represented at line 186.

Load cells 100 and 102 are represented with that numeration in FIG. 9. These load cells are each configured as a four resistance balanced bridge type load cell. The outputs of load cells 110 and 102 are directed to an amplification function as represented by respective lines 188 and 190 extending to amplifier block 192. The output of amplifier 192 is represented at line 194 extending to an analog-to-digital converter function represented at block 196. Correspondingly, output of the converter function 196 is directed to the microprocessor function 160 as represented at line 198. Microprocessor function 160 converts the signal to a force value in pounds which is displayed at the LCD 32. Each instruments or apparatus 10 is calibrated using 19 combinations of six standard weights. A best fit is determined, and the instrument must have a root mean square error (RMS) of 0.4 lb. or less to pass calibration. Once the calibration constants have been determined, the system is loaded with two redundant copies of the calibration constants. The zero point of the load cell and microprocessor assemblage is monitored at all times during the use of the apparatus 10. If a drift is found, then a warning is shown at the LCD display 32. If any lead wire to the load cell becomes disconnected, then the built-in monitoring detects this occurrence, shows an error message, and disables further use of the device 10 until the power is reset. These features ensure that the force reading shown is accurate and true. Absolute values of the outputs of the load cells 100 and 102 are summed to provide a force output signal. In general, the load measurement accuracy of device 10 is better than 0.1 lb.

Figure 10:
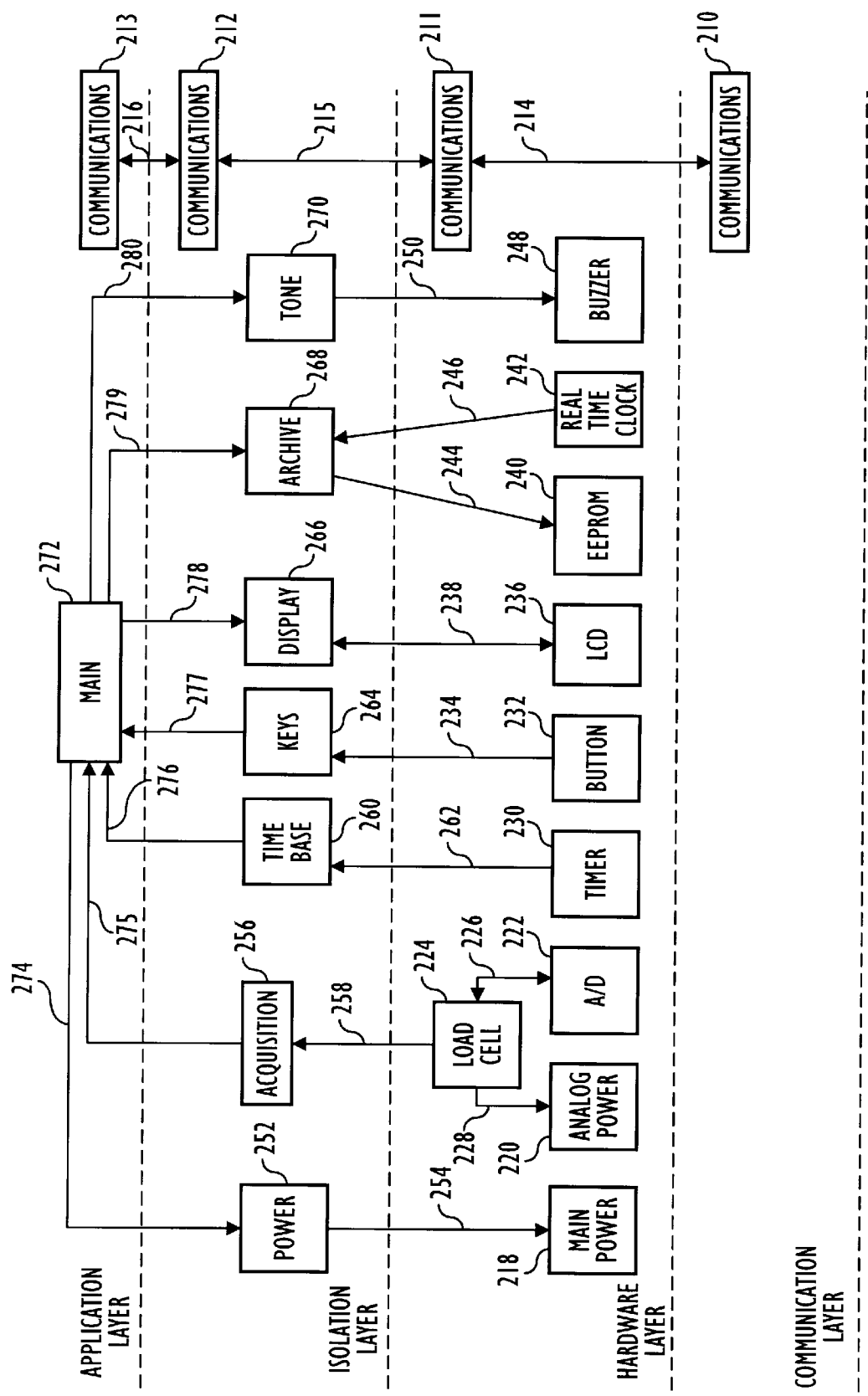
FIG. 10 is a functional drawing of the software program employed with the apparatus of FIG. 1.

Referring to FIG. 10, the control layout of the software employed with the apparatus is revealed in block diagrammatic fashion. Each block in the figure represents a control unit of software. Control software is provided in four distinct layers: (1) a communications layer; (2) a hardware interface layer, (3) an isolation layer; and (4) an application layer. All components use the same communications source code in the system. Note that one communications block 210 is in the communication layer. This block is responsible for receiving and transmitting packets of information through the communications hardware. It checks the incoming packets for proper formatting, data content, and proper termination. If these checks are passed, then the packet information is sent up the communication ladder to be processed by higher control blocks. This feature is at blocks 211–213 and associated dual arrows 214–216. The hardware interface layer is the first to process, which implements all of the electrical connections of the microprocessor to provide a separation of the control signal details from the functionality level of usage of the system resources. Looking to that layer, the main power is represented at block 218. This software block controls the action of a power transistor. When that transistor is held in a conducting condition, the power delivered inside the power regulator is maintained. When the main processing demands that the power be switched off, then this control block deactivates the transistor and power is removed. This control line is in parallel with a switch deemed a select switch as described at 36 in FIG. 1. The analog power software is represented at block 220. This software block controls the action of an analog section power transistor. When the transistor is held in a conducting condition, a regulated 5 v is connected to the analog components of the circuit including amplification, load cells, and the like. Software controlling all communications to and from the analog-to-digital converter is represented at block 222. Its association with the load cell treatment software is shown at block 224 as represented by dual arrow 226. Similarly, the control of analog power at the load cell is represented at arrow 228. Block 224 represents software controlling analog power and the function of collecting data from the load cells, including the application of calibration constants and maintenance of true force readings. When there is no need for a reading to be maintained, block 224 functions to switch off power applied to the analog section, thus conserving battery power. The tiring function is represented at block 230. This software component is driven by internal microprocessor hardware to activate every 2.5 milliseconds. From this timed interrupt, time-outs are counted and updated to provide the isolation layer with a consistent time base of operation. Switch monitoring function software is represented at button block 232. This software handles the recording of any presses of the two button switches 36 and 38 and is made available to the isolation layer for further processing as represented at arrow 234. An LCD software function is represented at block 236. This software handles the control signals required to send and read information to and from the liquid crystal display. Its association with the isolation layer is represented at arrow 238. Operation of the EEPROM function is represented at block 240. This EEPROM device records archival data. The software function at block 240 controls all of the data transfers to and from the memory device and provides the mechanism to confirm the data transfer before returning. Transfers are random access byte organized so that no assumptions need to be made regarding the size or configuration of the memory. Real time clock related software is represented at block 242. This software controls all data transfers to and from the real time clock in the circuit. The clock is a conventional chip device that is set for universal coordinated time (UTC) and runs on a lithium battery. Thus, the clock will continue to function in the absence of regulated 5 v supply. The function provides an arrangement for establishing time and date data saved in archival memory. An association of blocks 240 and 242 with the isolation layer is represented at respective arrows 244 and 246. Annunciator controlling software is represented at buzzer block 248. Its association with the isolation layer is represented at arrow 250.

The isolation layer functions to isolate the application layer from the hardware layer. In this regard, note that power associated software is represented at block 252 in association with hardware layer block 218 as represented at arrow 254. Software represented at block 252 handles the functionality of switching off main power to the apparatus 10. Before main power is switched off, any pending action by the main processing function is completed and stored to the archival memory. Then power may be switched off without loss of data. With this software, the device can, in effect, turn itself off, no intervention by the user being required. Software collecting raw load cell readings is represented by the acquisition block 256 and its association with the load cell software at block 224 is represented by arrow 258. The software represented at block 256 functions to generate a short running average. This average provides an improvement in signal-to-noise ratio and smoothes the responsiveness of the applied force to be displayed at the LCD display 32. The force value is held for the application layer to utilize. Time date software is represented at block 260 and its association with timer software 230 is represented at arrow 262. The software represented at block 260 provides the time control for other control blocks in the isolation layer. There also is a master time-out that is maintained for application layer utilization. Software reading switch or button presses from a hardware layer is represented at keys block 264. This software converts button presses into equivalent keystrokes for the application layer. The possible keystrokes are: select pressed (switch 36); menu pressed (switch 38); select held; menu held; both select and menu pressed; both select and menu held. Such keystrokes are held until the application layer makes use of them. The display software function is represented at block 266 and the software represented thereby formats data and sends it to the LCD hardware layer to be displayed. Custom characters are kept in this block and are transferred to the LCD when required This provides the application layer with display commands that know nothing of the hardware configuration.

Archival functioning software is represented at block 268. This software handles all interfacing. The hardware layer interfaces to the EEPROM and the real time clock. Such an arrangement allows the application layer to make simple requests and this software function will make proper space and size conversions and checks for purposes of storing information in the correct location. One related software is represented at block 270. This software allows the application layer to request that specific tones and hold times be made in conjunction with the annunciator. The timing of the on and off times for the annunciator power are tracked and counted by the time base block 260. This allows for a wide range of tones, warbles, and beeps to be sounded by a simple annunciator device.

The application layer controls all of the outward appearances and interactions of the apparatus 10. The user interface is driven from this point. Force levels, and exercise timings are controlled by this main program. Data saved to the archive memory is generated at this level and the configuration of user names and protocols are used in this software. This main software is represented at main block 272 which routine utilizes all of the isolation layer blocks to implement the functional requirements of apparatus 10 and its interaction with the user. The relationship of the main program at block 272 with the isolation layer is represented at arrows 274–280. Communications software represented at block 213 allows the communications ladder to have access to the application layer control blocks.

Figure 11:
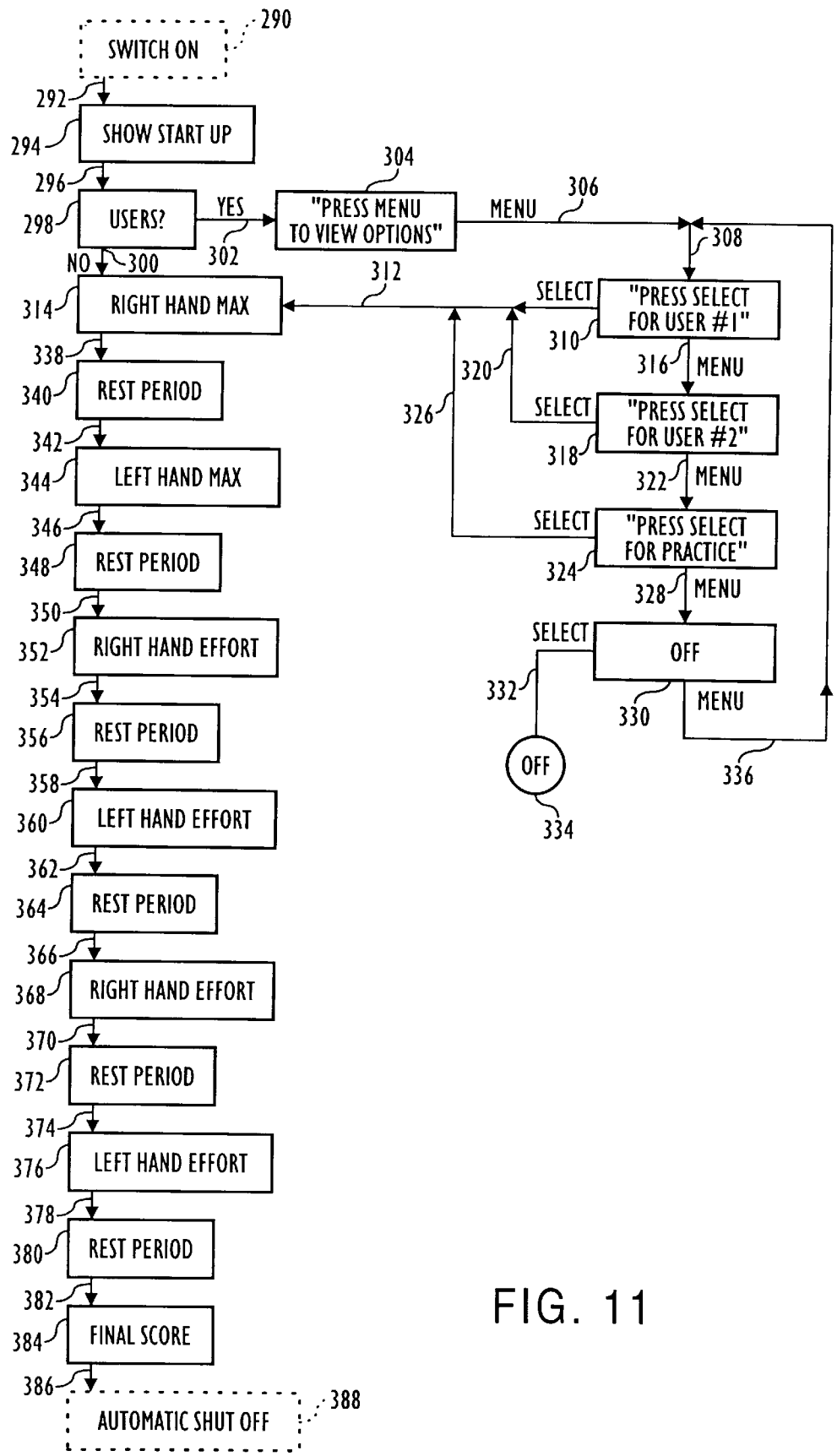
FIG. 11 is a flow chart showing an exercise regimen carried out by the apparatus of FIG. 1.

Referring to FIG. 11, a functional flow chart of the operation of apparatus 10 is provided. Each block in this flow chart represents an interaction with the user in connection with the principal isometric regimen protocol. Apparatus 10 is switched on by pressing the "select" button or switch 36. This activity is represented by dashed block 290. The protocol then continues as represented by arrow 292 and block 294 to show a start-up message at the LCD 32. Then, as represented at line 296 and block 298, a determination is made as to whether identified users have been configured into the apparatus 10. If not, then as represented a 300, the program immediately commences the exercise routine. Where user identification has been employed with the software, then as represented at line 302 and block 304, the user will be given a visual cue to press the "menu" button to review options, that switch or button being switch 38. A menu then is evolved as represented at lines 306 and 308 which extend to block 310. The user then may press the select button or switch 36 to elect an identification as user number 1. Once so selected, then as represented at line 312, the control system commences the exercise program as represented at block 314. Where the menu switch 38 is pressed again, then as represented at line 316 and block 318, the user is cued to press the select switch 36 to elect a second user. Where the select switch 36 then is depressed, as represented at lines 320 and 312, the apparatus 10 commences the programmed exercise. Pressing the menu switch 38 yet again as represented at line 322 and block 324 develops the visual cue indicating that the user may press the select switch 36 to carry out a practice routine. The practice routine is essentially the same as the identified user program, however, information developed such as maximum squeezing force for each hand and score is not submitted to archival memory. This practice routine starts by pressing select switch 36 as is represented at lines 326 and 312. Pressing the menu switch 38 again will provide for turning the apparatus 10 off as represented at line 328 and block 330. Apparatus 10 is then in an off state as represented by line 332 and node 334. As represented by loop line 336, apparatus 10 can be restarted by pressing the menu switch 38.

At the commencement of an exercise regimen or protocol intended for blood pressure control, the user is prompted with a visible cue to apply maximum squeezing force with the right hand. This force may be referred to as "maximum voluntary contraction" (PVC). As the user applies this squeezing contraction force, the apparatus times a sampling interval and provides a progressively enlarging bar graph as a visual indicator of the amount of compressive force being exerted. Additionally, the amount of that force is published at the LCD display 32 as it may vary during this MVC effort. The visual cuing not only provides the bar graph and instructions to squeeze hard, but it also signals the commencement of this interval for maximum effort squeezing with an audible cue. The maximum load value occurring during the effort represented at block 314 is submitted to memory and a target load value is computed by the microprocessor which preferably is 50% of MVC. Additionally, a threshold above that value is computed, for example, 62.5% of MVC. Following the right hand maximum squeeze effort, then as represented at line 338 and block 340, a rest period ensues. The visual cue provided during this rest period is one of a diminishing percentage from 100% of time, i.e. time remaining for the rest period. At the termination of the rest period, as represented at line 342 and block 344, an aural cue is given the user and a visual cue is provided telling the user to squeeze hard with the left hand. Thus, a left hand MVC or maximum load value is detected and recorded in memory. As before, during this maximum effort interval, a bar chart is published at the LCD 32 which increases in size as the squeezing compressive force or load values increase. Next, as represented at line 346 and block 348, a second rest period ensues and, as before, visual cuing is provided as a percentage of interval count down. At the termination of this rest period, as represented at line 350 and block 352, the user is given a visual and aural cue to provide a squeezing compressive force with the right hand which is at the computed target load value for the right hand. To aid the user during this subsequent target interval of time, an arrow point type center point visual cue is provided in connection with a dynamic bar graph wherein the top line of the bar graph will be present as a thin line in alignment with the center point arrow when the proper target squeezing force is applied. Additionally, the relationship between the applied load value and the target load value is presented in sequential time increments as a running score, 100% representing coincidence between the applied load value and the target load value. In the event the user applies compressive squeezing force above the noted upper threshold, for example of 62.5% of MVC, then an aural cue is sounded. In this regard, it is important that the target load value be maintained inasmuch as forearm blood flow appears to reach peak values at approximately 30 to 40% of MVC. At higher tensions, flow decreases. In this regard, see the following publication:

Humphreys, P. W., and A. R. Lind (1963). The Blood Flow Through Active and Inactive Muscles of the Forearm During Sustained Hand-Grip Contraction. J. Physio. (Lond.) 166, 120–135.

As represented at line 354 and block 356, the user now is cued to enter a rest period and, as before, the time remaining in the rest period is published at the visual display as percentage time remaining. Next, as represented at line 358 and block 360, the user is visually cued at the termination of the rest period to carry out a left-hand effort by applying squeezing compression at the target load value for a target load interval. As before, visual cuing with center point and bar graph are displayed during this effort and the noted running average score relating the relationship between the applied squeezing force and the target load value is displayed. At the end of this next target interval of time, as represented at line 362 and block 364, a next rest period ensues and the time remaining in that rest period is displayed as percentage of time remaining. As represented at line 366 and block 368 at the termination of the rest period, the user is visually cued to apply compressive squeezing force at the target load value with the right hand for a target interval. The center point and bar graph visual cue again is displayed along with the percentage of time remaining for this target interval. Additionally, as before, the score of the effort is displayed, 100% representing coincidence between the target load value and the applied compressive force. At the end of the target interval, as represented at line 370 and block 372, the user receives a visual cue that a rest period is under way and the percentage of time remaining in that rest period is displayed. As represented at line 374 and block 376, at the termination of this rest period, the user is provided a visual cue to carry out an effort squeezing the apparatus 10 to the noted target level load for a target interval. As before, the center point and bar graph are displayed during this effort and a running score is shown in addition to the percentage of time remaining in this target interval. As represented at line 378 and block 380, the apparatus 10 then times out a rest interval and displays the interval as a percentage of time remaining. The final running average score is then computed as represented at line 382 and block 384, 100% representing a perfect score. That score and the maximum right and left hand squeezing effort maximum values or MVC values are stored in archival memory and may be accessed by, for example, a trainer or attending physician. Storage of that data takes place in addition to time and date of entry data. Following the final display, as represented by line 386 and dashed boundary 388, apparatus 10 automatically shuts itself off.

Figure 12:
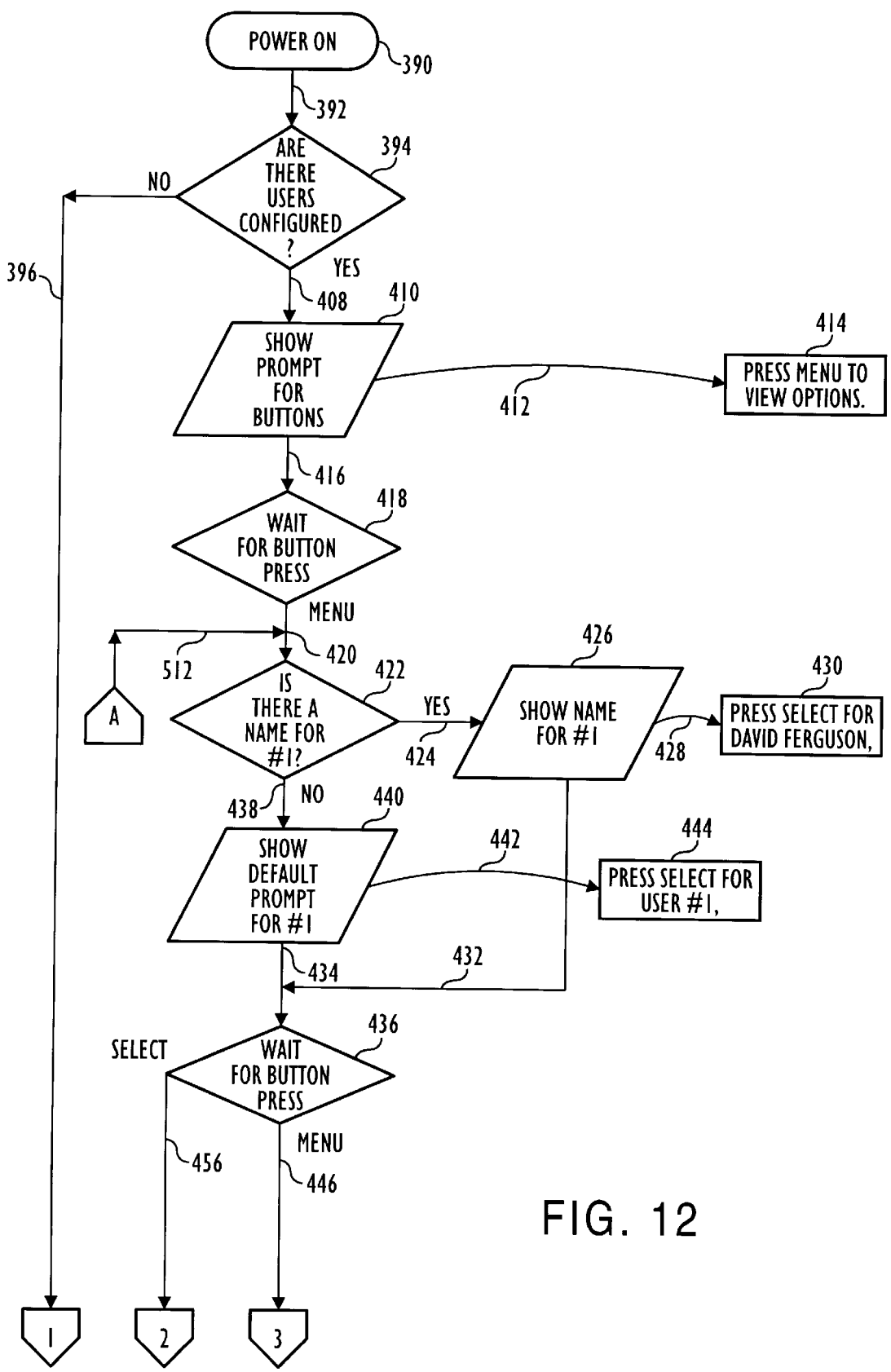
FIGS. 12–14 combine as labeled thereon to provide a flow chart showing a start-up procedure employed with the apparatus of the invention.
Figure 13:
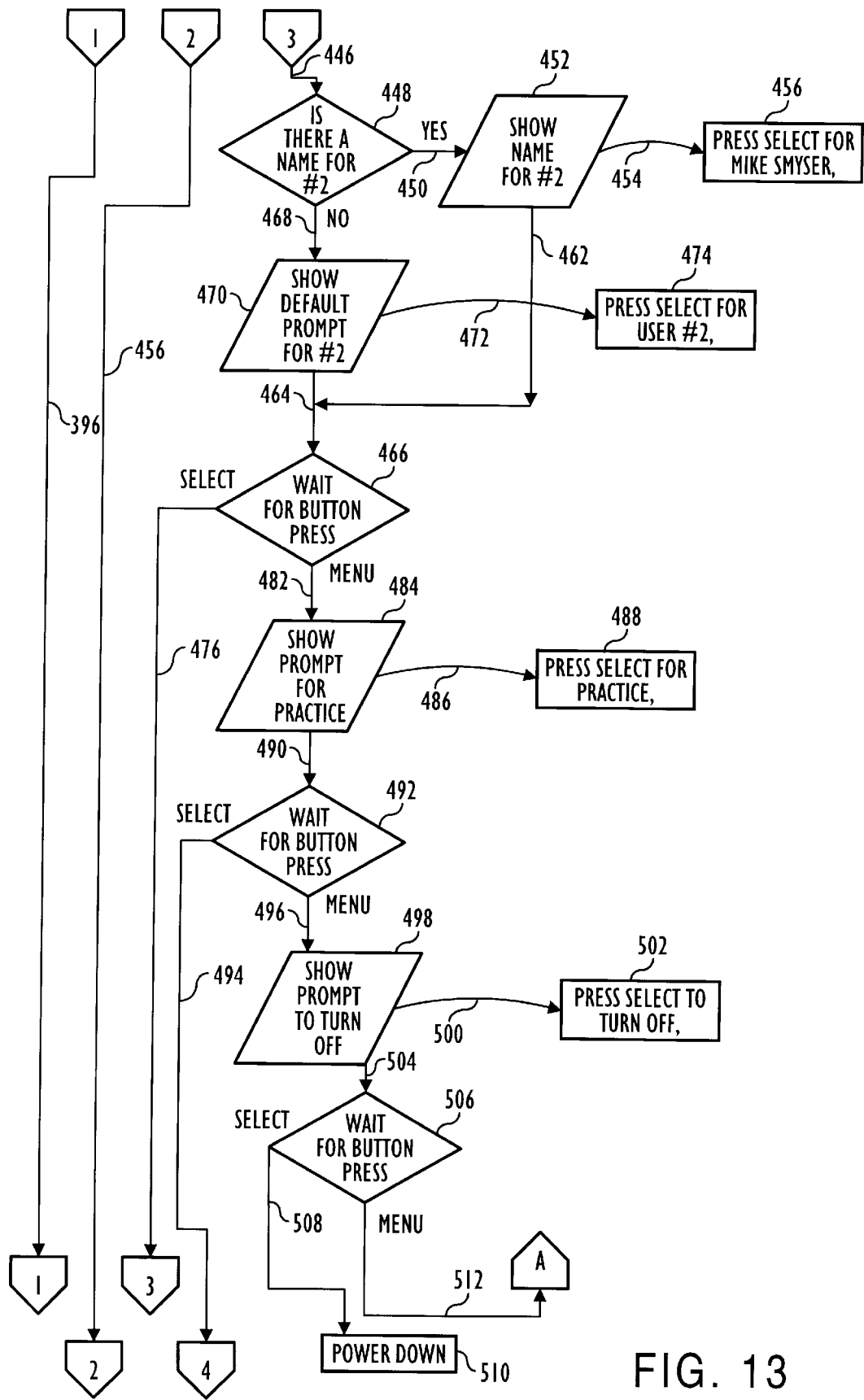
Figure 14:
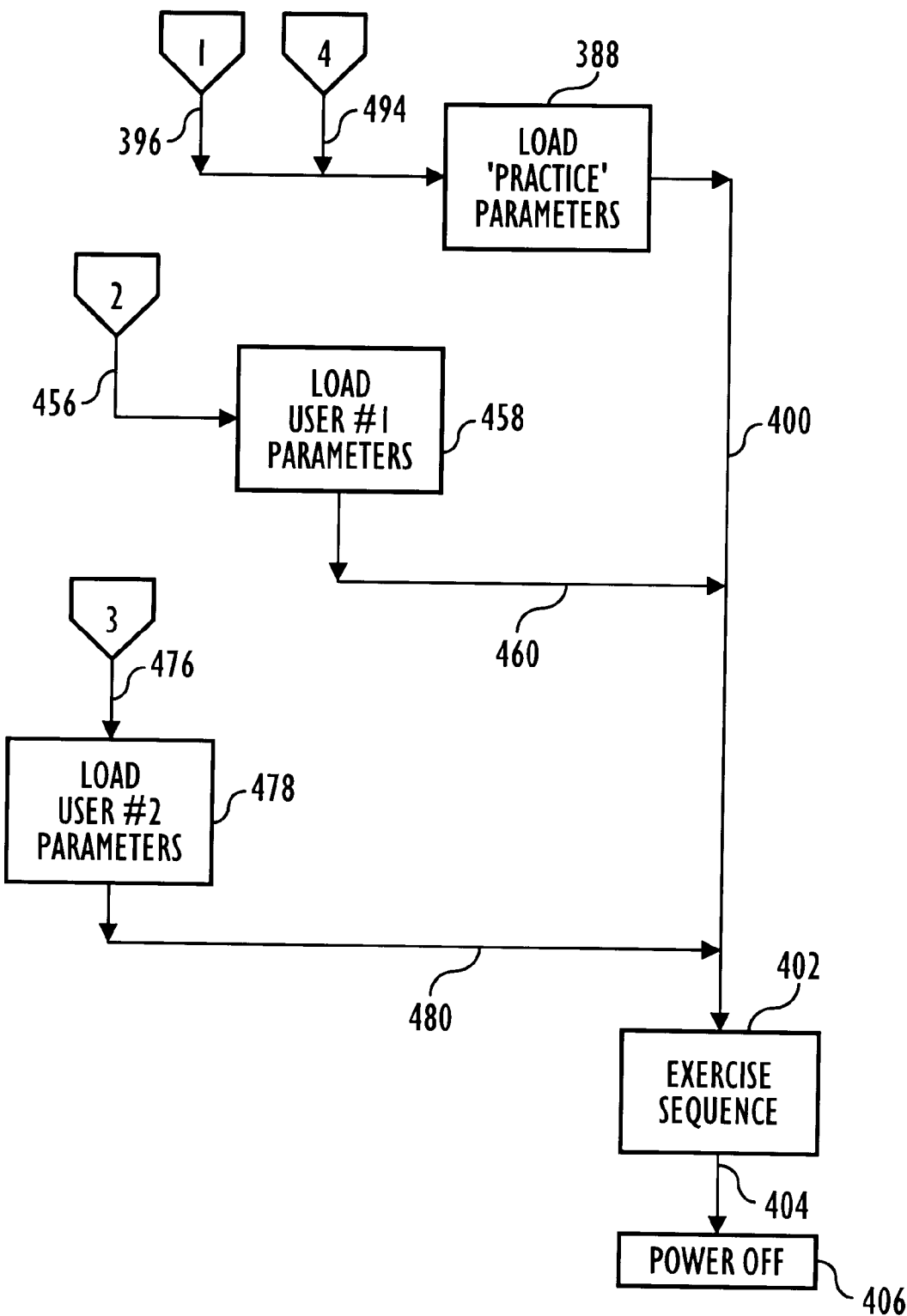

FIGS. 12–14 combine as numerically labeled thereon to provide a flow chart describing the initial operation of the apparatus 10 before the commencement of an exercise sequence. Looking to FIG. 12, power on is represented at node 390. With the application of power, as represented at line 392 and block 394, a determination is made as to whether there are users configured in the software. If there are none, then as represented by line 396 which extends to FIG. 14 and block 398, practice parameters are loaded and, as represented at line 400 and block 402, an exercise sequence ensues with those practice parameters. Following the exercise sequence, as represented at line 404 and block 406, power is turned off automatically. Returning to FIG. 12, where users are configured in the software then as represented at line 408 and block 410 a visual cue or prompt is provided instructing the user to press the menu switch 38 for options. This visual cue is represented by arrow 412 and display block 414. Next, as represented at line 416 and block 418, the program awaits the pressing of a button, i.e. the actuation of switch 38. Where the menu button is pressed, then as represented at line 420 and block 422, the program determines whether a name has been pre-programmed for a first user. Where that is the case, then as represented at line 424 and block 426, the individual whose name has been programmed in the apparatus 10 as a user is identified along with a cue to press the select switch 36. This visual cue is represented by arrow 428 and block 430. Then, as represented by lines 432, 434, and 436, the control awaits a button press, i.e. a pressing of the select switch 36. Where no individual's name has been programmed into the software, then as represented at line 438 and block 440, the system displays a default prompt for a user number 1. The display reads as represented at arrow 442 and block 444. Note in the latter block that a user number 1 is identified. Then, as noted above in conjunction with block 436, the system awaits a button press. Where the menu switch 38 has been pressed, then as represented at line 446 and block 448 in FIG. 13, a query is made as to whether there is a name for a second user. Where there is, then as represented at line 450 and block 452, that user's name is displayed in conjunction with a prompt to press the select switch.

Returning to FIG. 12, where the select button has been pressed in conjunction with block 436, then as represented at line 456, which extends to FIG. 1, the software loads user number 1 parameters as represented at block 458 and commences an exercise sequence as represented at lines 460, 400, and block 402.

Returning to FIG. 13, following the display as represented at block 456, the program continues as represented by lines 462, 464, and block 466, wherein the system awaits the press of either the select switch 36 or menu switch 38. Turning to block 448, in the event there is no name or a second user, then as represented at line 468 and block 470, a default to a user identified as number 2 is carried out. The display provided for this situation is represented at arrow 472 and block 474. In the latter regard, note that the display instructs the user to press the select switch 36 for carrying out a program with respect to a user identified as number 2. Returning to block 466, where the select switch 36 has been pressed, then the program proceeds as represented by line 476 and block 478 in FIG. 14 which provides for the loading of exercise parameters for a user designated as number 2. The program then continues as represented at lines 480, 400, and block 402 to carry out an exercise sequence.

Returning to block 466 in FIG. 13, where the menu switch 38 has been pressed, then as represented at line 482 and block 484, the program shows a prompt to the user for a practice exercise. The display provided by this prompt is represented by arrow 486 and block 488. Note that the display instructs the user to press the select switch 36 to commence a practice round. Then as represented by line 490 and block 492, the control system awaits a switch actuation. Where the select switch 36 has been pressed, then as represented at line 494 which extends to line 396 in FIG. 14, the system loads practice parameters as represented at block 398 and then enters the practice exercise sequence as represented at line 400 and block 402.

Returning to block 492 in FIG. 13, where the menu switch 38 has been actuated, then as represented at line 496 and block 498, the system displays a prompt to the user to turn it off by pressing select switch 36. This display is represented by arrow 500 and block 502. Then, as represented at line 504 and block 506, the system awaits a button press. Where the select switch 36 has been pressed, then as represented at line 508 and block 510, the system powers down. Where the menu switch 38 has been pressed, then as represented at line 512 which reappears in FIG. 12 leading to line 420, the program repeats with the query posed at block 422.

Figure 15:
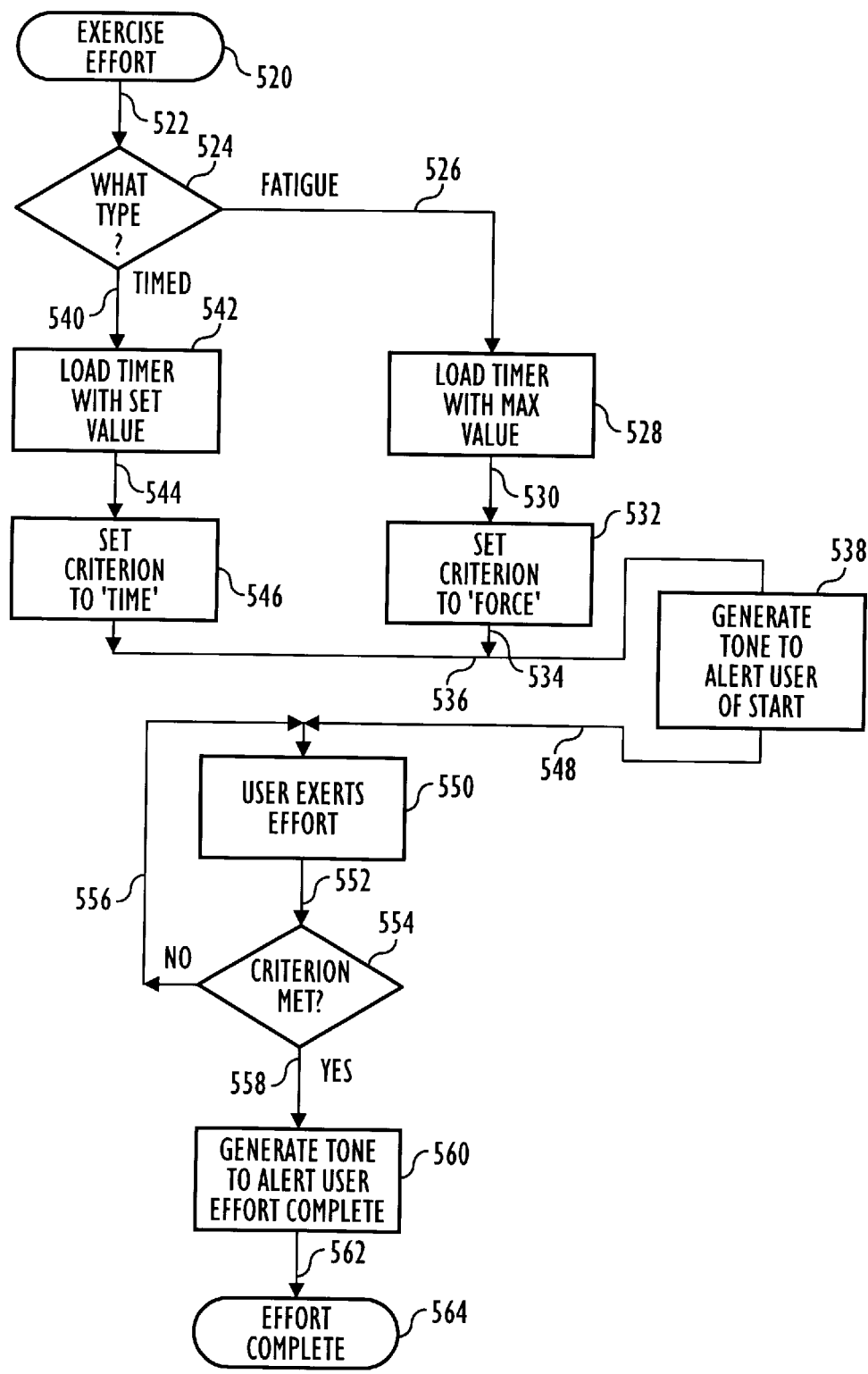
FIG. 15 is a flow chart demonstrating the exercise effort aspect of the apparatus of the invention for two types of exercise regimens.

Referring to FIG. 15, a flow chart describing that component of the control program wherein the type of exercise effort is elected is provided. In this regard, the conventional or standard exercise protocol is that described in connection with FIG. 11. However, the apparatus 10 also can be programmed, for example, to carry out a program wherein the grip is squeezed in compression for as long as the user is able to meet some target criteria. The length of time the user is able to meet that criteria is measured. Looking to the figure, the exercise effort is shown introduced at node 520, line 522, and block 524. At block 524, a determination is made as to what type exercise effort is involved. If it is a fatigue type effort, then as represented at line 526 at block 528, the system timer is loaded with a max value. That value may be, for example, 4 ½ minutes. Then, as represented at line 530 and block 532, the criterion is set to a force based exercise effort. Then, as represented at lines 534 and 536 and block 538, a tone is generated to alert the user to start the exercise.

Returning to block 524, where a standard or timed exercise is at hand, then as represented at line 540 and block 542, the system timer is loaded with set time values, for example maximum effort intervals, rest intervals, and target intervals. Then, as represented at line 544 and block 546, the criterion is set to a time based exercise and the program continues as represented at line 536 and block 538. Following the generation of an audible cue to alert the user of the start of the program, as represented at line 548 and block 550, the user is called upon to exert effort. This effort continues as represented at line 552 and block 554 until the established criterion is met. Where the criterion is not met, then as represented by loop line 556, the exercise continues. Where the criterion is met, then as represented at line 558 and block 560, the system generates a tone to alert the user that the effort is complete. The program then exits as represented at line 562 and node 564.

Figure 16:
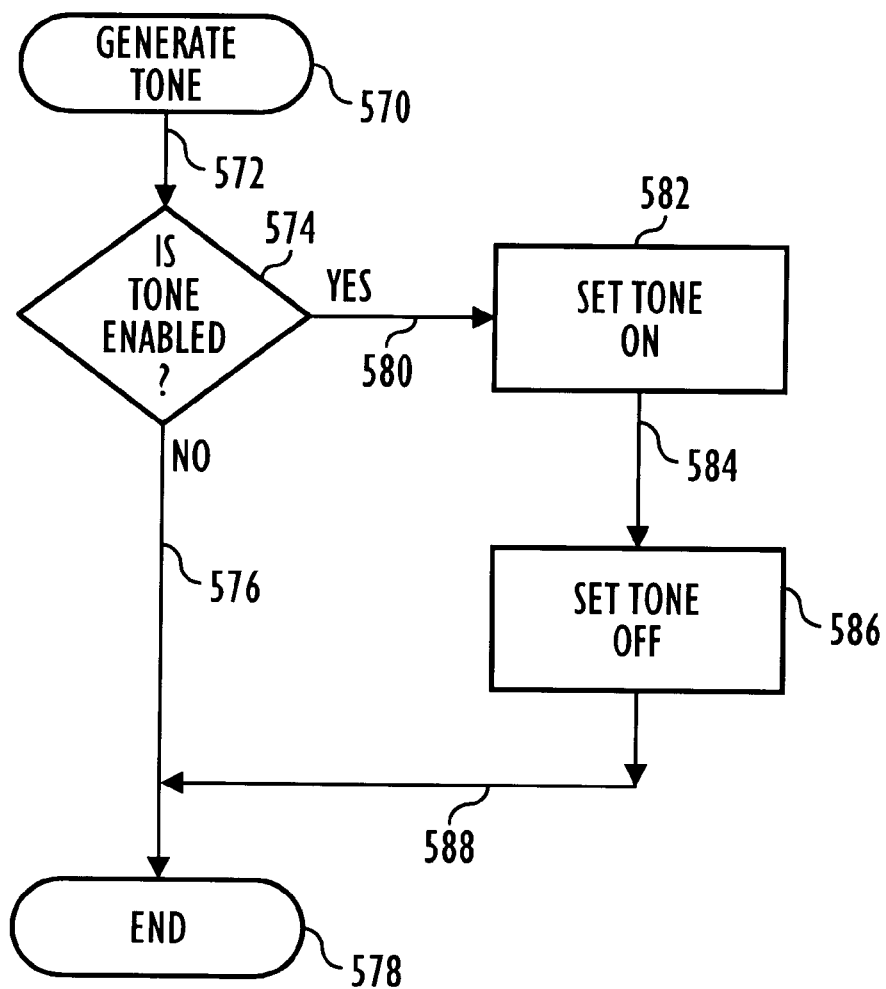
FIG. 16 is a flow chart showing a routine for generating a tone by the apparatus of the invention.

Referring to FIG. 16, a routine for providing a tone or audible cue is represented in flow chart fashion. In general, the tone feature is enabled. In this regard, where the apparatus 10 is to be used in an environment where no noise is desired, then the tone can be blocked through the enabling feature. In the figure, the tone generation routine is entered at node 570 and, as represented at line 572 and block 574, a determination is made a to whether the tone feature has been enabled. If it has not, then as represented at line 576 and node 578, a routine is ended and no tone is generated. Where the tone has been enabled, then as represented at line 580 and block 582, the tone is set on, and, as represented at line 584 and block 586, following a short tone interval, the tone is turned off and the routine ends as represented at line 588.

Figure 17:
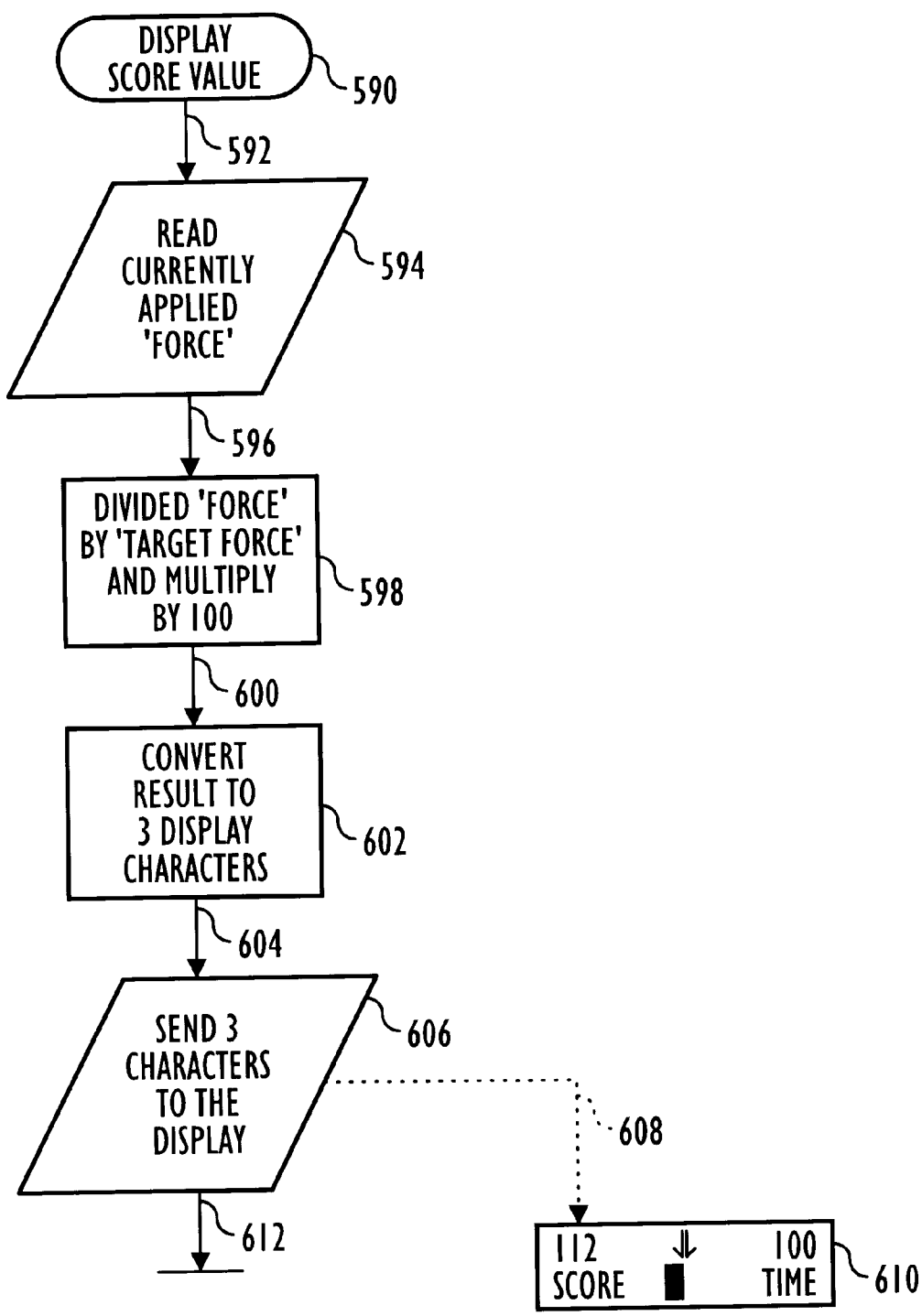
FIG. 17 is a flow chart demonstrating the technique by which a score value is developed by the apparatus of the invention.

Referring to FIG. 17, a routine for deriving and displaying score values is illustrated in flow chart fashion. This program is entered at node 590 and commences as represented at line 592 and block 594 to determine or read the currently applied force or load values as the user attempts to match the target force value. Then, as represented at line 596 and block 598, the score is determined by dividing that read force by the precomputed target force and multiplying by 100 to provide the score as a percent. This score is developed for sequential increments of time, preferably each increment representing 1% of the time interval occurring during the application of target related forces. As represented at line 600 and block 602, the score is converted to three display characters. Then, as represented at line 604 and block 606, three characters representing score are sent to the display. The score may be above or below 100%. A representative display is shown in conjunction with dashed arrow 608 and block 610. Note that the score shown is above 100% and a bar chart is shown extending beyond a center point arrow to represent that the user is above the target load value desired. The routine then is ended as represented at line 612.

Figure 18:
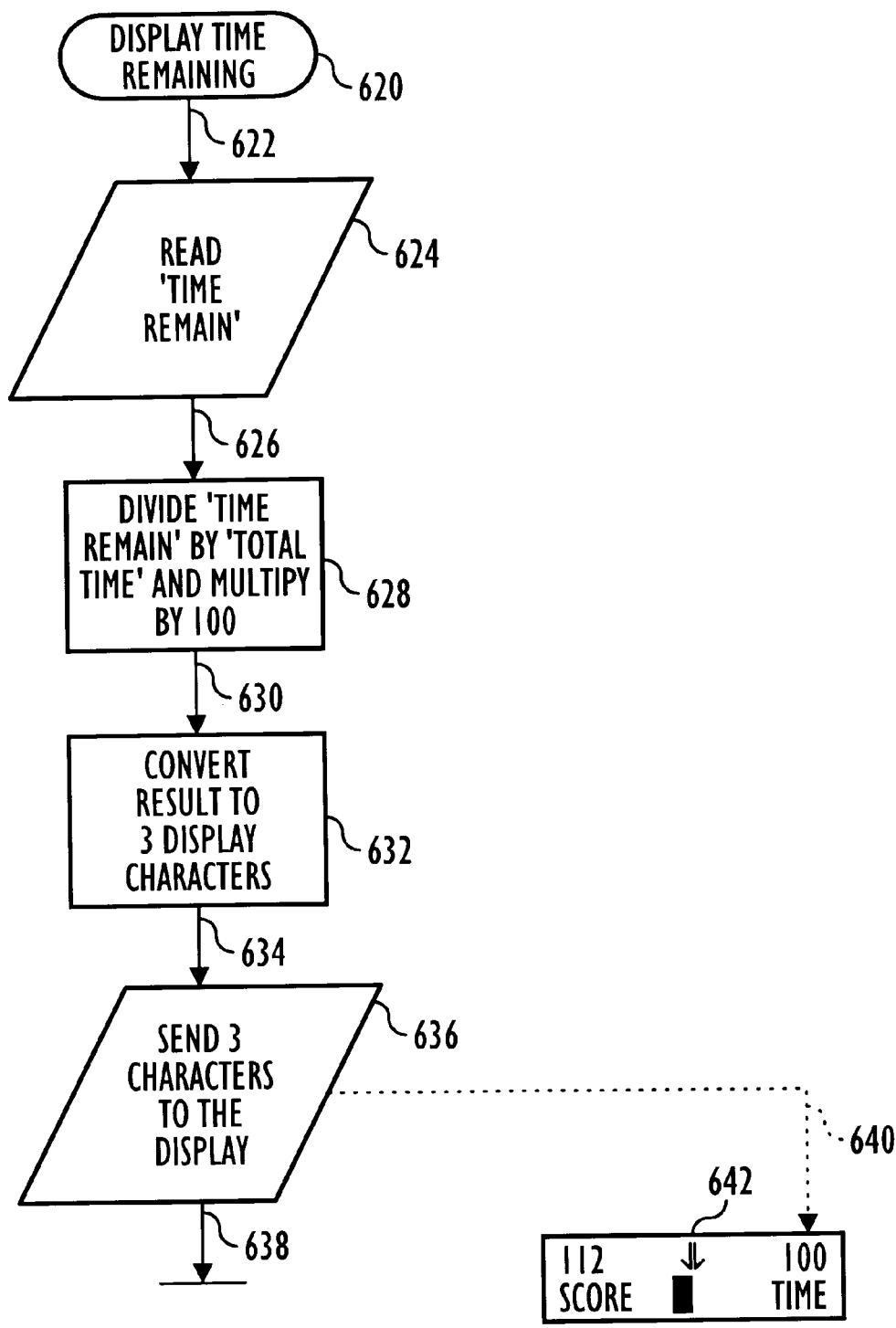
FIG. 18 is a flow chart demonstrating the technique by which interval time is developed and displayed by the apparatus of the invention.

As noted earlier, the interval of time readout provided to the user is one which is established as a percent of the configured interval at hand, for example a rest interval or a target timing interval. By showing the time remaining as a remaining percentage interval, the apparatus 10 may be utilized in a placebo fashion, for example in clinical trials. Referring to FIG. 18, a routine providing for the display of time remaining is seen commencing at node 622. As represented at line 622 and block 624, the system reads the time remaining in a given interval. Then, as represented at line 626 and block 628, the time remaining is divided by the total time of interval and the result is multiplied by 100 to derive a percentage valuation. Then, as represented at line 630 and block 632, the percentage or result is converted to three display characters. Then, as represented at line 634 and block 636, those three characters are sent to the display and the general program continues as represented at line 638. The display is illustrated by dashed arrow 640 and block 642. For the display at block 642, note that the time is shown at the commencement of an interval as 100%.

Figure 19:
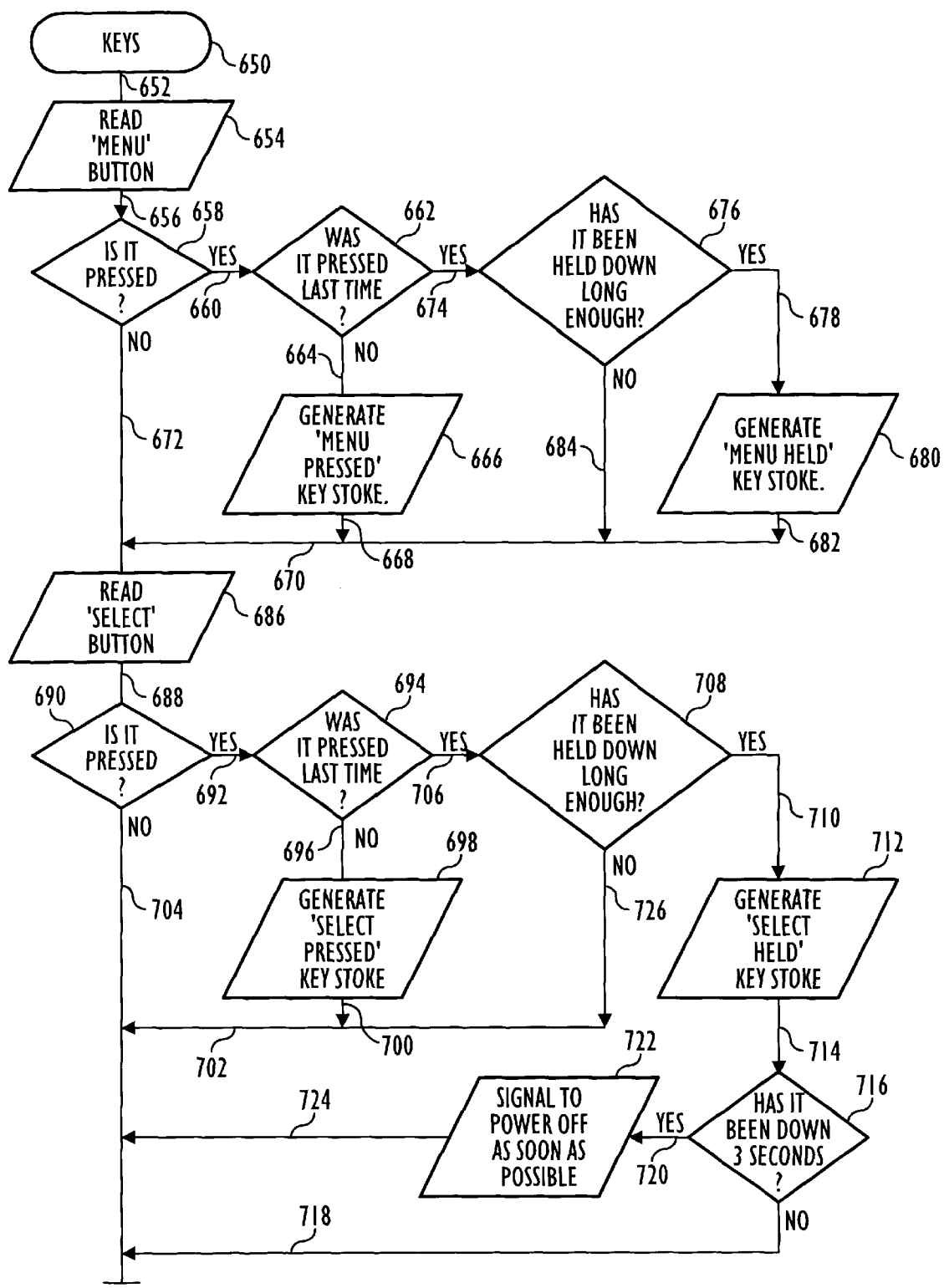
FIG. 19 is a flow chart demonstrating the acquisition of keystroke data by the apparatus of the invention.

Referring to FIG. 19, a flow chart describing the system's handling of buttons or switches 36 and 38 is set forth in flow chart fashion. In general, a keystroke for each of the switches is defined as one which is instantaneous or is one wherein the switch is held down for an interval of time, for example greater than one second. In FIG. 19, this component of the control commences at node 650 and line 652 wherein the instructions at block 654 provide for the reading of the "menu" switch 38. Then, as represented at line 656 and block 658, a determination is made as to whether that button was pressed, i.e. the switch was actuated. In the event that it was pressed, then as represented at line 660 and block 662, a determination is made as to whether that switch 38 was pressed at the last look. Where that is not the case, then, as represented at line 664 and block 666, a "menu pressed" keystroke is generated and the program continues as represented by lines 668, 670, and 672. Where the query posed at block 662 results in an affirmative determination, then as represented at line 674 and block 676, a determination is made as to whether the button or switch has been held down long enough to generate a "menu held" keystroke. Where that is the case, then as represented at line 678 and block 680, the system generates a "menu held" keystroke. The program then continues as represented at line 682 and line 670. Where the menu button has not been held down long enough, then as represented at lines 684 and 670, the program continues.

Returning to block 658, there a determination is made that the menu button or switch 38 has not been pressed, then as represented at line 672 and block 686, the program reads the "select" button which is switch 36. Then, as represented at line 688 and block 690, a determination is made as to whether switch 36 has been pressed. In the event that it has been pressed, then as represented at line 692 and block 694, a determination is made as to whether the switch 36 was pressed the last time. In the event that it was not, then as represented at line 696 and block 698, a "select pressed" keystroke is generated. The program then continues as represented at lines 700, 702, and 704.

Where the query posed at block 694 results in an affirmative determination, then as represented at line 706 and block 708, a determination is made as to whether the switch or button 36 has been held down long enough, for example longer than one second. In the event that it has, then as represented at line 710 and block 712, the program generates a "select held" keystroke. Then, as represented at line 714 and block 716, a determination is made as to whether the button has been held down for three seconds. In the event that it has not, then the program continues as represented at lines 718 and 704. Where the select button has been held down three seconds, then the user has determined to manually turn off apparatus 10. Accordingly, with an affirmative determination at block 716, then as represented at line 720 and block 722, the program provides a signal to power off. The program then continues to line 704 as represented at line 724. Where the select button has not been held down long enough, then as represented at lines 726 and 702, no "select held" keystroke is generated and the program continues as represented at lines 726 and 702.

Figure 20:
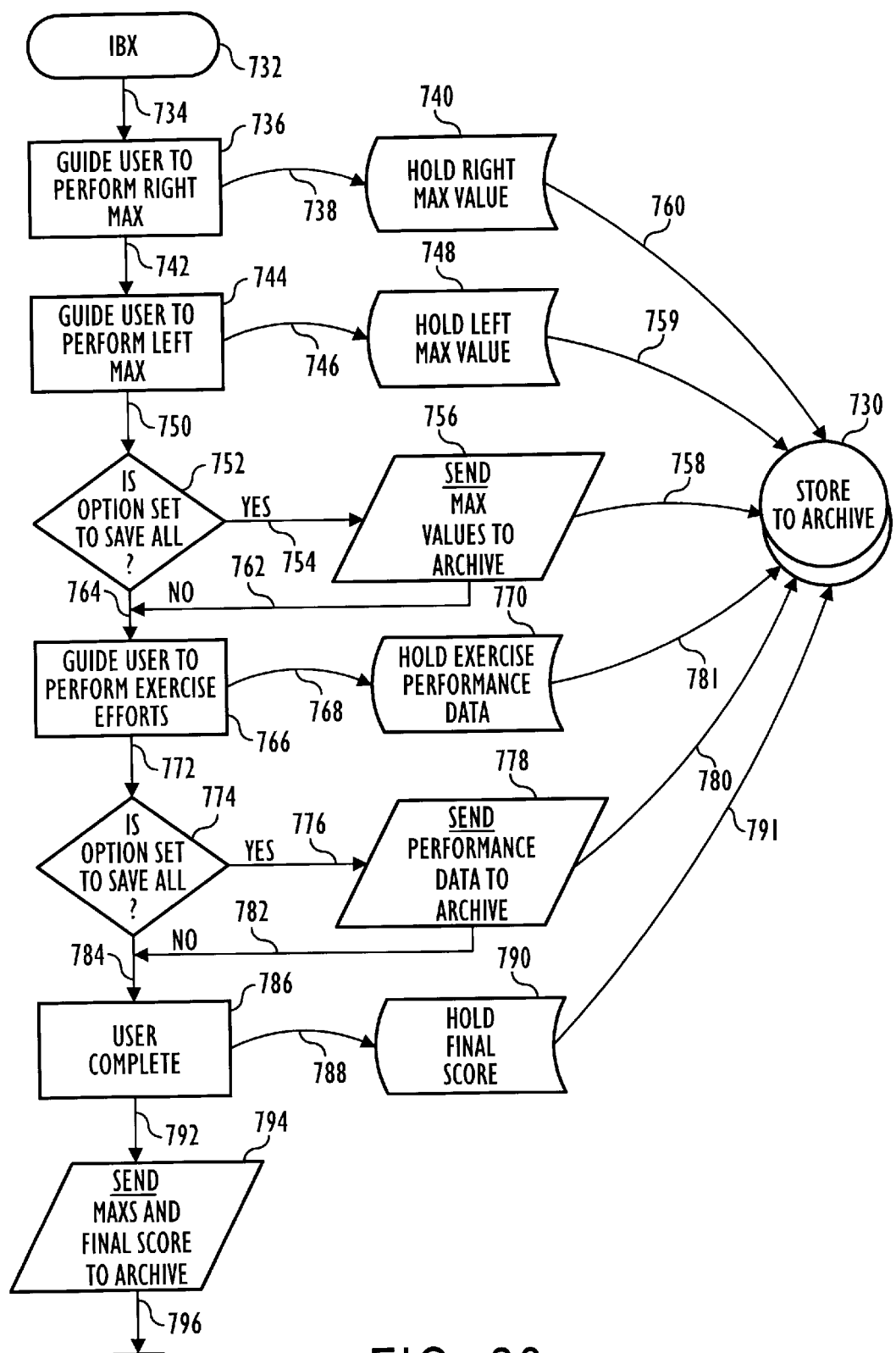
FIG. 20 is a diagram demonstrating the technique by which certain data are stored in archival memory.

Referring to FIG. 20, a diagram is provided describing the utilization of temporary and archival memory by the apparatus 10. In the figure, archival memory is represented at the symbol 730. The program is seen commencing at node 732 and line 734 leading to block 736. Block 736 provides for guiding the user to apply a maximum squeezing force with the right hand. That value of MVC then is held in temporary volatile memory as represented by arrow 738 and block 740. Next, as represented at line 742 and block 744, the user is guided to perform a maximum compressive squeezing effort with the left hand. The highest value of that effort then is stored in temporary memory as represented at arrow 746 and block 748. The program may be configured to save these maximum load values in archival memory. Accordingly, the figure shows line 750 leading to the query at block 752 determining whether the system has been programmed to save those values. In the event that it has been so programmed, then as represented at line 754 and block 756, the maximum values are stored in archival memory as represented by lines 758–760. The program then continues as represented at lines 762 and 764. Where the system has not been programmed to save those max values, then as represented at line 764 and block 766, the user is guided to perform the exercise effort. The results of those efforts, for example in terms of score and force value, are submitted to temporary memory as represented by arrow 768 and block 770. The system then continues as represented at line 772 and block 774 wherein a determination is made as to whether the system has been configured to save the exercise efforts represented at block 766. In the event that is the case, then as represented at line 776 and block 778, the performance data is submitted to archival memory 730 as represented at arrows 780 and 781. The program then continues as represented at lines 782 and 784 where the option is not set to save all of the performance data. Then as represented at line 784 and block 786, when the user has completed the exercise regimen, as represented at arrow 788 and block 790, the final score, which is a running average is held in temporary memory. The program then continues as represented at line 792 and block 794. At this block, the program sends the maximum or MVC values and the final score to archival memory 730 and continues as represented at line 796. A submittal of the final score from temporary memory to the archival memory 730 is represented at arrow 891.

Figure 21:
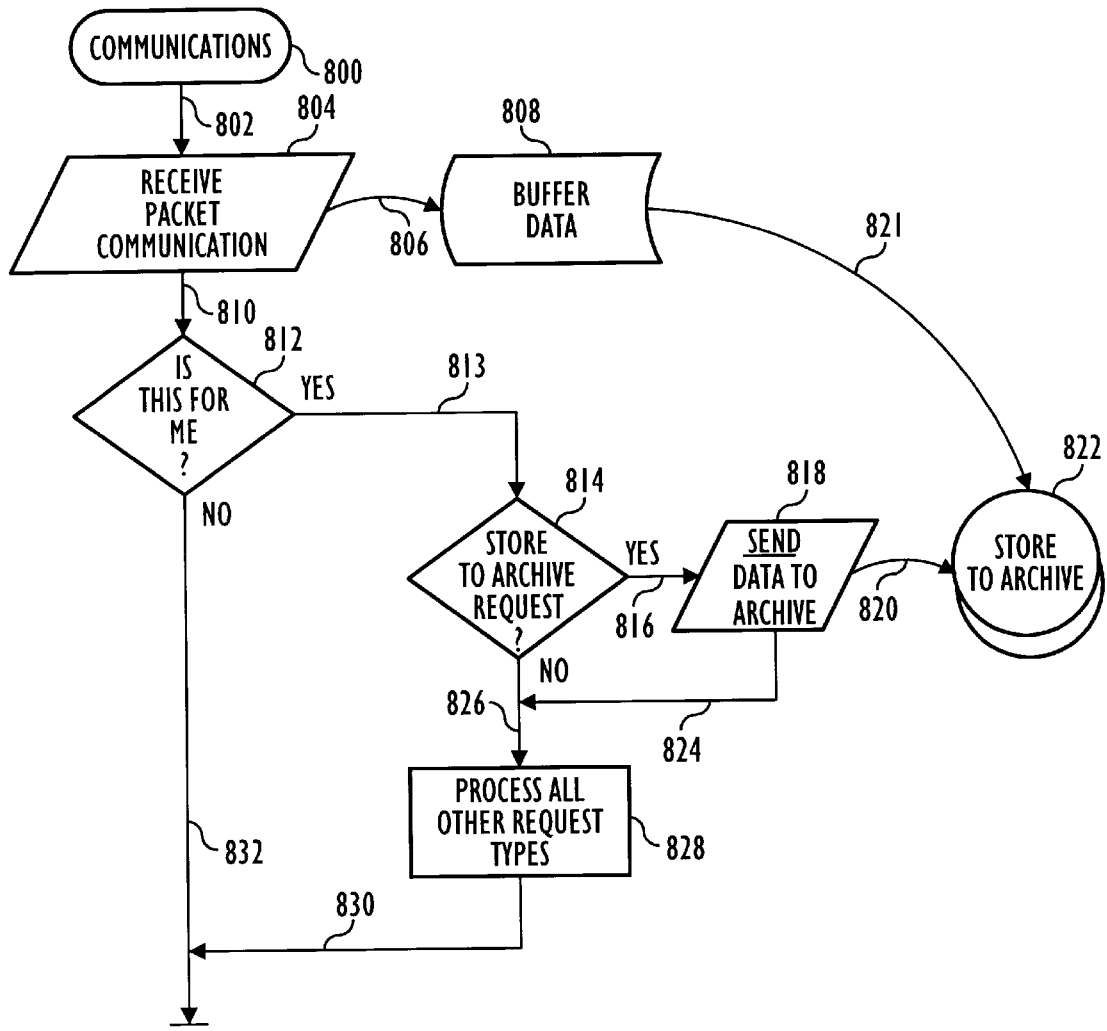
FIG. 21 is a flow chart describing the assertion of externally received communication data and submittal thereof to archival memory.

Apparatus 10 has the capability of receiving certain data through communications port 46 and storing it in archival memory. For example, for some applications, it is desirable to store blood pressure data in conjunction with the carrying out of the exercise regimen. Referring to FIG. 21, a communications flow chart is provided. This sequence commences with node 800 and line 802 leading to block 804. Block 804 provides for the reception of a communications packet which, as represented at arrow 806 and block 808, is retained in buffer memory. The routine continues as represented at line 810 and block 812 where a determination is made as to whether the communication packet is intended for the apparatus 10 at hand. In the event that it is, then as represented at line 813 and block 814, where a request is made to archivally store the communicated data, then as represented at line 816 and block 818, the data is sent to archival storage as represented by arrows 820 and 821, and symbol 822. The program then continues as represented at lines 824 and 826 to process all other request types as represented at block 828. The program then continues as represented at lines 830 and 832. Where the packet communication was not intended for the instrument at hand, then the program continues as represented at line 832.

Figure 22:
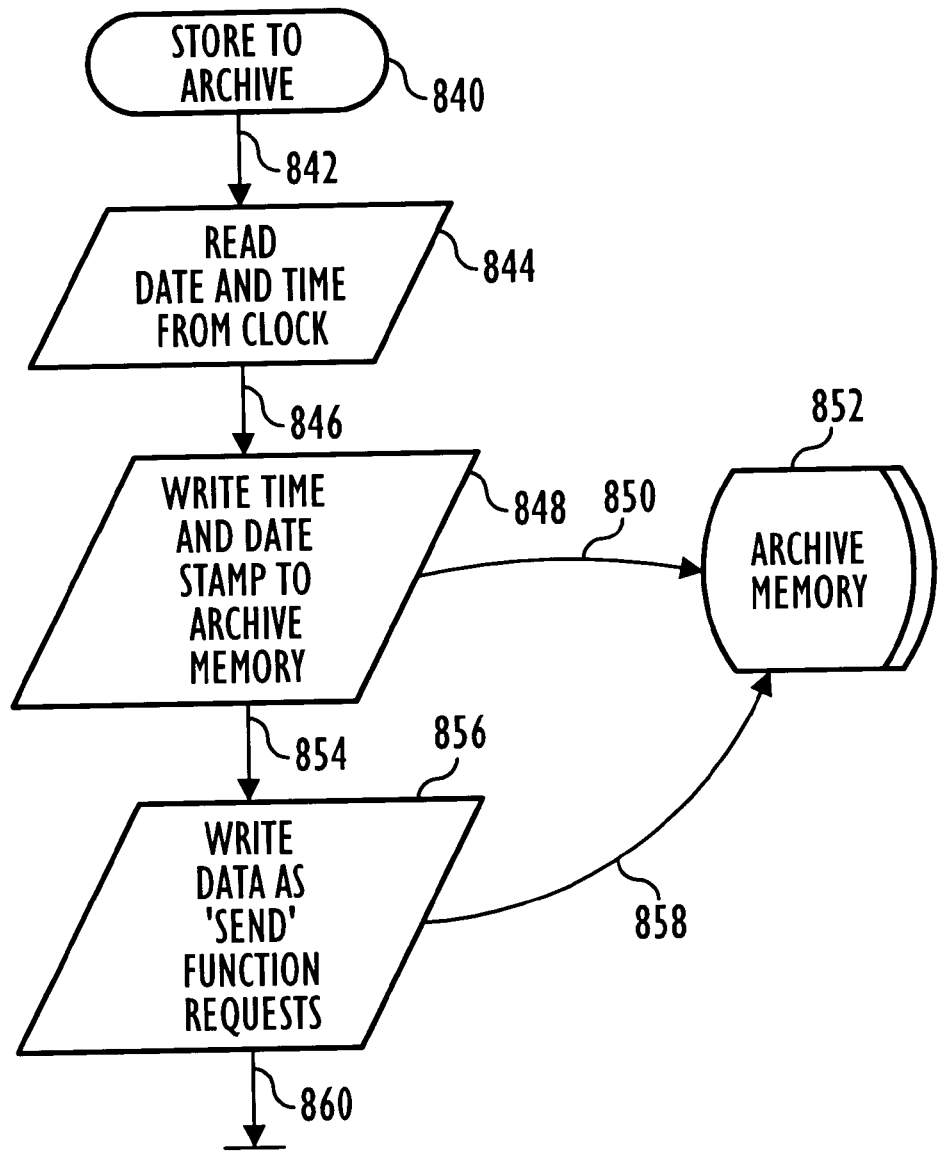
FIG. 22 is a flow chart describing the submittal of time and date data to archival memory.

Referring to FIG. 22, a routine for storing data in archival memory is portrayed. The routine commences as represented at node 840 and line 842. At block 844, the program reads the date and time from the clock component of the circuitry. For each insertion into archival memory, that information is supplied whether or not the data was received from an external source or was generated internally. Accordingly, the writing of time and date information to archival memory is represented at arrow 850 and the archival memory is represented at symbol 852. The routine continues as represented at line 854 and block 856, the latter block providing a writing of the requested data into archival memory 852 as represented by arrow 858. The routine continues as represented at line 860.

Figure 23:
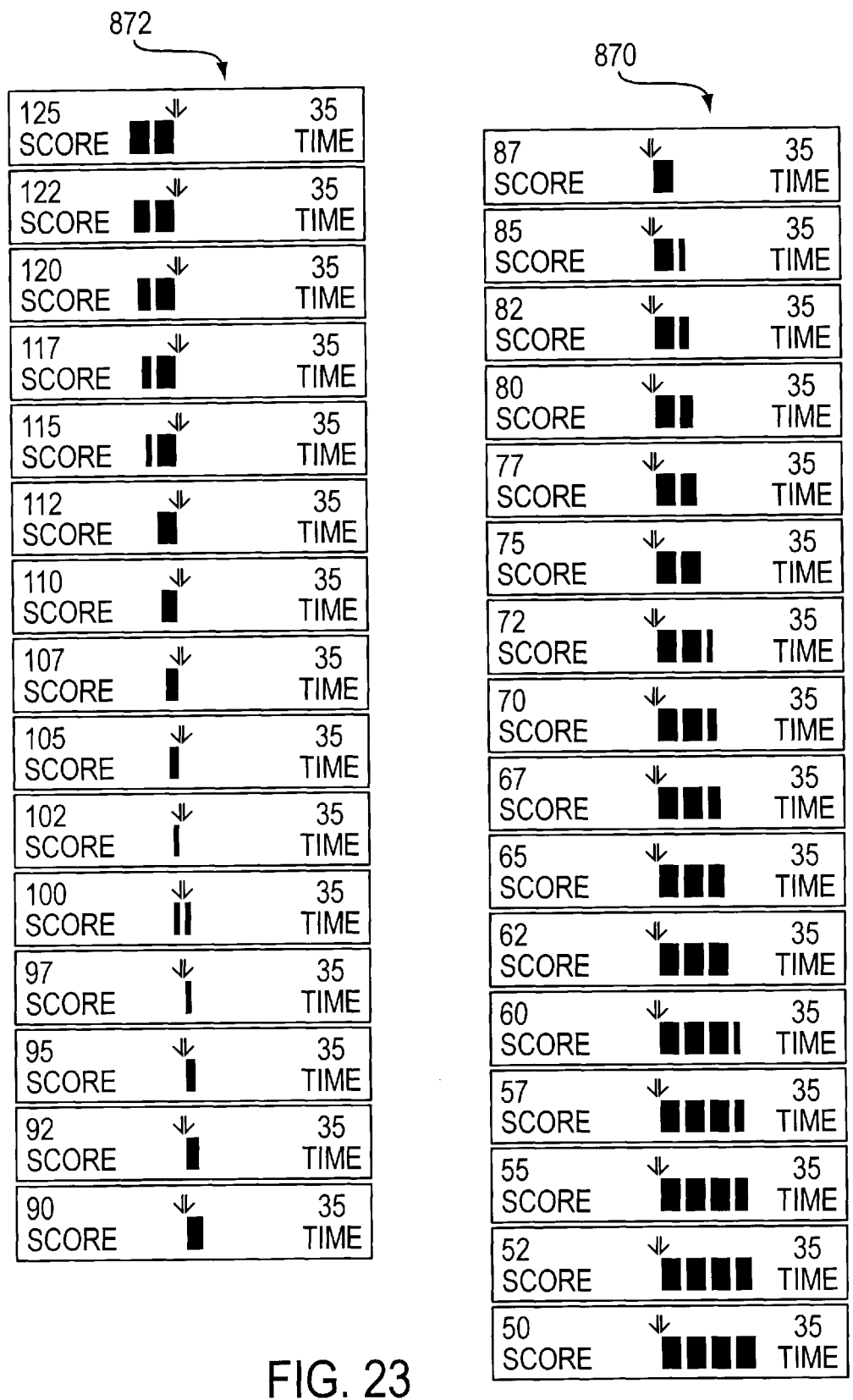
FIG. 23 shows a sequence of displays which may be developed by the apparatus of the invention during a target interval of exercise effort.

Referring to FIG. 23, the visual cuing at the LCD display 32 during a target interval exercise is portrayed. In the figure, time is frozen at 35% remaining. In the sequence shown in general at 870, one may observe that where a score is 50%, a dynamic bar chart is developed extending below a center point represented as a dual line arrow. In this regard, the components of the bar chart are thick as the score deviates from 100%. Note that the bar chart at a score of 87% is thickened and falls a shorter distance below the center point arrow than at a 50% score. Looking to the sequence shown in general at 872, one may observe that as the score approaches 100%, the line representing the top of the bar graph becomes thin and is in alignment with the center point at 100%. As the user applies excessive compressive force, the bar chart moves above the center point and becomes thicker in correspondence with the amount of deviation above the center point. When the pressure exerted by the user exceeds an upper threshold level, ten an audible tone is generated to cue the user to drop compressive squeezing pressure target level. On the other hand, when the pressure supplied represents a low score below a given lower threshold, then the display as represented at sequence grouping 870 transitions from a steady state one to a blinking one.

Figure 24:
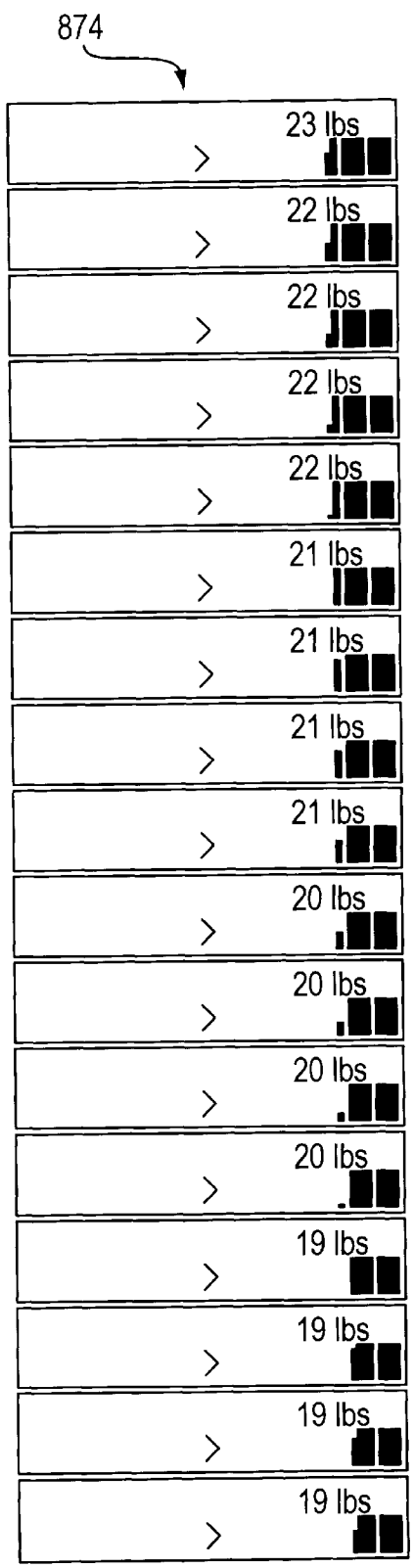
FIG. 24 is a sequence of displays which may be provide during a maximum effort interval by the apparatus of the invention.

Referring to FIG. 24, a sequence of demonstrative displays is represented at 874 as they may occur during a maximum or MVC effort. A bar graph is developed which expands from right to left in the sense of the figure, however, it is built pixel-by-pixel, becoming thicker in a line-by-line fashion as the maximum pressure builds. In this regard, one line of the dynamic bar graph is two pounds and the user will be able to observe the bar graph build in pixel increments of ¼ pound. As is apparent, the display also shows the actual number of pounds in equal pound increments applied as a compressive squeezing force by the user.

Since certain changes may be made in the above apparatus, system and method without departing from the scope of the invention herein involved, it is intended that all matter contained in the above description or shown in the accompanying drawings shall be interpreted as illustrative and not in a limiting sense.

We claim:

1. Apparatus for carrying out a protocol-based isometric exercise regimen using the hand, comprising:

a rigid housing having a hand grasping portion including a first hand graspable portion having an outer curved multiple finger receiving surface and an inwardly disposed first alignment channel, a second hand graspable portion spaced from said first graspable portion having an outwardly disposed load input opening, grip side portions extending between said inward graspable portion and said portion to define a grip cavity, and an interacting portion fixed to and extending forwardly from said hand grasping portion;

an elongate, rigid circuit supporting panel having a first elongate edge mounted in stress transfer relationship upon said inwardly disposed alignment channel and extending within said grip cavity to a second elongate edge adjacent said load input opening;

a load cell assembly having a base positioned in stress transfer relationship upon said circuit supporting panel second elongate edge and extending outwardly through said second graspable portion load input opening, an elongate outer force component located over said base and dimensioned in correspondence with a widthwise extent of a palm region of said hand, and a load cell component mounted intermediate said base and said outer force component, having a force output signal in response to the compressive transfer of force between said load cell assembly, said first hand graspable portion and said panel;

a control circuit within said housing, responsive to said force output signal to provide an evaluation output; and a readout assembly mounted at said housing interaction portion responsive to said evaluation output to provide a perceptible output corresponding therewith.

2. The apparatus of claim 1 in which said load cell assembly base includes an inwardly disposed second alignment channel positioned over said panel second elongate edge.

3. The apparatus of claim 1 in which:
said load cell assembly base is configured having a lengthwise extent between first and second end regions along said panel second edge corresponding with the widthwise extent of the palm region of said hand, and having respective first and second load cell mounts at said first and second end regions;

said load cell component includes first and second load cells mounted at respective first and second load cell mounts and extending mutually inwardly in cantilever fashion along said load cell assembly base; and said elongate outer force component includes a centrally disposed force input pedestal connected in force transfer relationship to the mutually inwardly disposed ends of said first and second load cells.

4. The apparatus of claim 1 in which said second hand graspable portion includes a flexible grip mounted upon said elongate outer force component.

5. The apparatus of claim 4 in which said flexible grip is shaped with a pistol grip configuration, and having an inwardly disposed grip cavity slideably positionable over said elongate force component and at least a portion of said load cell assembly base.

6. The apparatus of claim 1 in which said rigid housing interacting portion comprises:
an input portion including a switch input surface extending forwardly from adjacency with said second graspable portion;

first and second hand actuable switches supported adjacent said input surface; and a readout portion having a display support surface extending from adjacency with said input portion and sloping at a reading angle therefrom for locating said readout assembly in an orientation effective to enhance the readability thereof when said hand grasping portion is grasped.

7. The apparatus of claim 6 in which said reading angle is about 45 degrees.

8. The apparatus of claim 6 in which:
said interacting portion readout portion and input portion are configured to define an enclosed forward cavity;

said control circuit is mounted upon said panel and includes a microprocessor, memory, a real time clock, an amplifier function responsive to said load cell component force output to derive an amplified force output signal, and an analog-to-digital converter responsive to said amplified force output signal to derive a digitized force output;

said first and second hand actuable switches are electrically coupled with said microprocessor by flexible leads extending to said panel; and said readout assembly is electrically coupled with said microprocessor by flexible leads extending to said panel.

9. The apparatus of claim 8 in which:
said control circuit includes a communications driver circuit;

including a data communications terminal mounted within said forward cavity; and said communications terminal is electrically coupled with said microprocessor by flexible leads extending to said panel.

10. A system for carrying out a protocol based isometric exercise regimen by a user, comprising:
a hand grip component including a load cell assembly responsive to compressive squeezing force applied by a hand of said user to derive a load value corresponding with said force;

a display, responsive to a display input signal to provide a visually perceptible display output;

a controller including a processor, memory, and a first switch hand actuable to provide a start input;

said processor being responsive to said start input to access said memory and derive a said display input signal providing a grip squeezing first visual cue to said user, responsive to subsequent corresponding first said load values to retain them in said memory and to derive a said display input signal providing a second visual cue corresponding with the values thereof, responsive to access a target load factor from said memory and to a maximum one of said first load values to derive a first target load value as a predetermined percentage of said maximum one of said first load values and to retain said target load value in said memory, responsive to derive a said display input signal providing a grip squeezing third visual cue to said user to apply said squeezing force at said first target load value for a predetermined first target interval, responsive to subsequent second said load values to carry out timing of said predetermined first target interval and to derive score values for each of a sequence of timing increments generated during said first target interval, said score values corresponding with a comparison of said second load values with said first target load value, and responsive to said score values to derive a display input signal providing a display output representing said score values, responsive at the termination of said first target interval to derive a said display input signal providing a target interval termination third visual cue.

11. The system of claim 10 in which:
said first visual cue indicates that the user is to provide a maximum squeezing effort;

said processor is responsive to access a maximum effort interval value from said memory and to determine said maximum one of said first load values at the termination of said maximum effort interval; and said processor is responsive to record said maximum one of said first load values in said memory.

12. The system of claim 10 in which said processor is responsive to derive each said timing increments as a percentage of time of said first target interval remaining and to derive a said display input signal providing said interval termination third visual cue as a zero percentage of interval countdown.

13. The system of claim 10 in which said processor is responsive to derive said score values as a percentage of said target load value and to derive a first target interval score value, and is responsive to record said maximum one of said first load values as retained data and said target interval score value in said memory.

14. The system of claim 13 in which:
   said controller includes a calendar circuit for deriving a date output; and
   said processor is responsive to said date output to effect the recordation thereof in said memory in conjunction with the said recording of said maximum one of said first load values as retained data and said target interval score value.

15. The system of claim 14 in which:
   said controller includes a data transfer port connectable with an interactive data communications system; and
   said processor is responsive to an input from said interaction data communication system to download said retained data and score values from said memory into said data communications system from said transfer port.

16. The system of claim 10 in which said processor is responsive to said derived score values to derive a said display input signal providing a center pointer visual cue representing said target load value, and a target effort dynamic bar graph visual cue having a top position present as a top line aligned with said center pointer when a said second load value equals said target load value, said top line moving away from said center pointer when a said second load value deviates from said target load value.

17. The system of claim 16 in which said processor derives said display input signal providing said target effort dynamic bar graph wherein said top line progressively expands in width when said second load values correspondingly progressively deviate from said target load value.

18. The system of claim 10 in which said processor is responsive to said first load values to derive a said display input signal providing a maximum effort dynamic bar graph visual cue having a height corresponding with each said first load values and being generated as a sequence of abutting lines, each of which is formed of displayed pixels, each said pixel corresponding with a predetermined load value.

19. The system of claim 16 in which:
   said controller includes an annunciator responsive to an annunciator input to generate a sound output; and
   said processor is responsive to a said second load value exceeding a predetermined upper effort threshold having an upper threshold load value above said target load value to derive said annunciator input.

20. The system of claim 16 in which said processor is responsive to a said second load value less than a predetermined lower effort threshold having a lower threshold load value below said target load value to alter said display input signal generating said center point visual cue from a steady-state condition to a blinking condition.

21. The system of claim 10 in which said processor derives said display input signal generating said grip squeezing first visual cue as identifying the use of a given hand of said user, said processor is responsive to access a first maximum effort interval value from said memory to determine a maximum one of said first load values at the termination of said maximum effort interval; said processor is responsive at the termination of said first maximum effort interval to derive a said display input signal providing a display output as a fourth visual cue identifying the presence of a first rest interval, is responsive to access said memory for the time related value of said first rest interval and to carry out the tiring thereof, is responsive at the termination of a time-out of said first rest interval to derive a said display input signal providing a grip squeezing fifth visual cue identifying the use of the other hand of said user opposite said given hand, responsive to subsequent corresponding said load values occurring during a second maximum effort interval to derive a said display input signal providing a sixth visual cue corresponding with the values thereof, responsive to access a said target load factor from said memory and a maximum one of said third load values from said memory to derive a second target load value as a predetermined percentage of said maximum one of said third load values and to retain said target load value in said memory, responsive at the termination of said second maximum effort interval to derive a said display input signal providing a display output as a visual cue identifying the presence of a second rest interval, responsive to access said memory for the time related value of said second rest interval and to carry out the timing thereof.

22. The system of claim 21 in which said processor is responsive at the termination of said second rest interval to derive a said display input signal providing said grip squeezing third visual cue to said user to apply with said given hand said squeezing force for said predetermined first target interval at said first target load value.

23. The system of claim 22 in which said processor is responsive at the termination of said first target interval to derive a said display input signal providing a display output as a seventh visual cue to said user identifying the presence of a third rest interval, and is responsive to access said memory for the time related value of said third rest interval and to carry out the timing thereof.

24. The system of claim 23 in which said processor is responsive to the termination of said third rest interval to derive a said display input signal providing a display output as a grip squeezing eighth visual cue to said user to apply with said opposite hand said squeezing force at said second target load level for a predetermined second target interval, responsive to subsequent fourth said load values to commence timing said predetermined second target interval and to derive score values for each of a sequence of timing increments generated during said second timing interval, said score values corresponding with a comparison of said fourth load values with said second target load value, and responsive to said score values to derive a display input signal providing a display output representing said score values.

25. The system of claim 23 in which said processor derives said score values as a running average score value.

26. The system of claim 25 in which said processor is responsive to record in said memory said maximum one of said first load values, said maximum one of said third load values, and the finally derived said running average score value.

27. A method for carrying out an isometric exercise by a user, comprising the steps of:
   (a) providing a hand grip and display instrument, the hand grip component thereof including a load responsive assembly having load value outputs in response to compressive squeezing force applied by a hand of the user, the display component thereof being responsive to a display input to provide a display output visually perceptible to said user, said instrument having memory and an interactive communications port;
   (b) cuing said user at said display to apply a maximum effort squeezing said hand grip component with a given hand;
   (c) then monitoring subsequent said load value outputs for a maximum effort interval;
   (d) recording a maximum load value corresponding with one of said load value outputs monitored in step (c) in said memory;

(e) determining a first target load value as a predetermined percentage of said maximum load value for said given hand;

(f) cuing said user at said display to rest for a first rest interval;

(g) at the end of said first rest interval, cuing said user at said display to apply a maximum effort squeezing said hand grip component with another hand opposite said given hand;

(h) then monitoring subsequent said load value outputs for a maximum effort interval;

(i) recording a maximum load value corresponding with one of said load value outputs monitored in step (h) in said memory;

(j) determining a second target load value as a predetermined percentage of said maximum load value recorded in step (i);

(k) cuing said user at said display to rest for a second rest interval (l) cuing said user at said display to apply a said squeezing force with said given hand at said first target load value for a target interval of time;

(m) then monitoring subsequent said load value outputs occurring during said target interval of time;

(n) cuing said user at said display during said step (m) of the comparative relationship between said load value outputs occurring during said target interval of time and said first target load value based upon increments of time;

(o) deriving score values during said monitoring step (m), said score values corresponding with a comparison of said load value outputs with said first target load value;

(p) cuing said user at said display to rest for a third rest interval;

(q) cuing said user at said display to apply a said squeezing force with said hand opposite said given hand at said second target load value for a target interval of time;

(r) then monitoring subsequent said load value outputs occurring during said target interval of time;

(s) cuing said user at said display during said step (r) of the comparative relationship between said load value outputs occurring during said target interval of time and said second target load value based upon increments of time;

(t) deriving score values during said monitoring step (r), said score values corresponding with a comparison of said load value outputs with said second target load value; and (u) recording in said memory a recording score value corresponding with said score values.

28. The method of claim 27 including step:

(v) recording the date of occurrence of steps (d), (i), and (h) in said memory.

29. The method of claim 28 including the step:

(w) downloading the data recorded in memory in conjunction with steps (d), (i), (h), and (v) from said interactive communications port to a remote data receiving facility.

30. The method of claim 27 in which said steps (c) and (h) include the step of displaying a maximum effort dynamic bar graph visual cue at said display having a height corresponding with each said load value output and being generated as a sequence of abutting lines, each of which is formed of displayed pixels, each such pixel corresponding with a predetermined load value.

31. The method of claim 27 in which said recording score value of step (u) corresponds with a running average of said score values.

32. The method of claim 27 in which said steps (n) and (s) are carried out by providing as a visual cue, a center point representing a respective said first and second target load value, and a target effort dynamic bar graph having a top position present as a top line aligned with said center point when a said load value output corresponds in equality with respective said first and second target load value, said top line moving away from said center point when a respective said first and second target load value deviates from said target load value.

33. The method of claim 32 in which said target effort dynamic bar graph top line is caused to progressively expand in width when said load values correspondingly deviate from said first and second target load values.

34. The method of claim 27 in which:

said step (a) includes the provision of an annunciator for generating a sound cue;

said step (l) includes the step of generating said sound cue when said load value exceeds a predetermined upper effort threshold having an upper threshold load value above said first target load value; and said step (s) includes the step of generating said sound cue when said load value exceeds a predetermined upper effort threshold having an upper threshold load value above said second target load value.

35. The method of claim 27 in which said step (f) cuing said user to rest for a first rest interval, and said step (k) cuing said user to rest for a second interval are carried out by displaying sequential timing increments as a percentage of respective such first and second interval.

36. The method of claim 27 in which said step (n) cuing said user during said target interval of time based upon increments of time and said step (s) cuing said user during said target interval of time based upon increments of time include time readout cues displaying said increments of time as percentages of said target intervals of time.

* * * * *